US011529322B2

(12) United States Patent
Phanstiel, IV et al.

(10) Patent No.: US 11,529,322 B2
(45) Date of Patent: Dec. 20, 2022

(54) SPERMINE PRO-DRUGS

(71) Applicant: UNIVERSITY OF CENTRAL FLORIDA RESEARCH FOUNDATION, INC., Orlando, FL (US)

(72) Inventors: Otto Phanstiel, IV, Orlando, FL (US); Mukund Pandurang Tantak, Orlando, FL (US); Houssine Ikhlef, Orlando, FL (US)

(73) Assignee: UNIVERSITY OF CENTRAL FLORIDA RESEARCH FOUNDATION, INC., Orlando, FL (US)

( * ) Notice: Subject to any disclaimer, the term of this patent is extended or adjusted under 35 U.S.C. 154(b) by 85 days.

(21) Appl. No.: 16/922,626

(22) Filed: Jul. 7, 2020

(65) Prior Publication Data

US 2021/0000769 A1    Jan. 7, 2021

Related U.S. Application Data

(60) Provisional application No. 62/871,161, filed on Jul. 7, 2019, provisional application No. 63/028,439, filed on May 21, 2020.

(51) Int. Cl.
| | | |
|---|---|---|
| *A61K 31/165* | (2006.01) | |
| *A61K 9/00* | (2006.01) | |
| *A61K 31/155* | (2006.01) | |

(52) U.S. Cl.
CPC .......... *A61K 31/165* (2013.01); *A61K 9/0019* (2013.01); *A61K 9/0053* (2013.01); *A61K 31/155* (2013.01)

(58) Field of Classification Search
CPC .................................................. A61K 31/165
See application file for complete search history.

(56) References Cited

U.S. PATENT DOCUMENTS

2006/0122279 A1* 6/2006 Burns .................. A61K 31/132
514/626

OTHER PUBLICATIONS

Morrell et al. CAS: 166: 485293, 2016.*
Muth et al. CAS: 160: 182712, 2014.*
Agostinelli, E. et al., "The biological functions of polyamine oxidation products by amine oxidases: Perspectives of clinical applications", Amino Acids, 2004, vol. 27, pp. 347-358.
Albert, Jessica S. et al., "Impaired osteoblast and osteoclast function characterize the osteoporosis of Snyder-Robinson syndrome", Orphanet Journal of Rare Diseases, 2015, vol. 10, No. 27, pp. 1-13.
Bolkenius, Frank N. et al., "Specific inhibition of polyamine oxidase in vivo is a method for the elucidation of its physiolical role", Biochimica et Biohysica Acia, 1985, vol. 838, pp. 69-76.
Carpino, Louis A. Carpino et al., "Reductive Lactonization of Strategically Methylated Quinone Propionic Acid Esters and Amides", J. Org. Chem., 1989, vol. 54, No. 14, pp. 3303-3310.
Murray-Stewart, Tracy et al., "Polyamine Homeostasis in Snyder-Robinson Syndrome", Med. Sci., 2018, vol. 6, No. 112, 13 pages.
Cason, A Lauren et al., "X-linked spermine synthase gene (SMS) defect: the first polyamine deficiency syndrome", European Journal of Human Genetics, 2003, vol. 11, pp. 937-944.
Cervelli, Manuela et al., "Inhibition of acetylpolyamine and spermine oxidases by the polyamine analogue chlorhexidine", Journal of Enzyme Inhibition and Medicinal Chemistry, 2013, vol. 28, No. 3, pp. 463-467.
De Alencastro, G. et al., "New SMS mutation leads to a striking reduction in spermine synthase protein function and a severe form of Snyder-Robinson X-linked recessive mental retardation syndrome", J Med Genet, 2008;vol. 45, pp. 539-543.
Dias, Gleiston G. et al., "Quinone-based fluorophores for imaging biological processes", Chem. Soc. Rev., 2018, vol. 47, pp. 12-27.
Di Paolo, Maria Luisa et al., "Exploring the activity of polyamine analogues on polyamine and spermine oxidase: methoctramine, a potent and selective inhibitor of polyamine oxidase", Journal of Enzyme Inhibition and Medicinal Chemistry, 2019, vol. 34, No. 1, 740-752.
Feng, Xiangjun et al., "Mild and Efficient Synthesis of N 1,N 5,N 10-Tri-tertbutoxycarbonyl Spermine", Synthetic Communications, vol. 42, No. 2, pp. 247-278.
Gahl, William A. et al., "Reversal by aminoguanidine of the inhibition of proliferation of human fibroblast by spermidine and spermine", Chemico-Biological Ineractions, Jul. 1978, vol. 22, issue 1, pp. 91-98.
Ikeguchi, Yoshihiko et al., "Aminopropyltransferases: Function, Structure and Genetics", J. Biochem., 2006, vol. 139, No. 1, pp. 1-9.
Wang, Xiaojing et al., "Spermine Synthase Deficiency Leads to Deafness and a Profound Sensitivity to Difluoromethylornithine", The Journal of Biological Chemistry, Jan. 9, 2009, vol. 284, No. 2, pp. 930-937.
Jensen, John R. et al., "Polyamines Stimulate Mitochondrial Calcium Transport in Rat Brain", Journal of Neurochemistry, 1987, vol. 48, No. 3, pp. 765-772.
Johnson-Ajinwo, Okiemute Rosa et al., "Stable Isotope Dilution Gas Chromatography—Mass Spectrometry for Quantification of Thymoquinone in Black Cumin Seed Oil", J. Agric. Food Chem., 2014, vol. 62, pp. 5466-5471.
Li, Chong et a., "Spermine synthase deficiency causes lysosomal dysfunction and oxidative stress in models of Snyder-Robinson syndrome", Nature Communications, 2017, vol. 8, No. 1257, 15 pages.
Massaro, Chelsea et al., "Investigation of Polyamine Metabolism and Homeostasis in Pancreatic Cancers", Med. Sci., 2017, vol. 5, No. 32, 14 pages.
Minocha, Subhash C. et al., "High-performance liquid chromatographic method for the determination of dansyl-polyamines", Journal of Chromatography, 1990, vol. 511, pp. 177-183.

(Continued)

*Primary Examiner* — Rei Tsang Shiao
(74) *Attorney, Agent, or Firm* — Timothy H. Van Dyke; Wolter, Van Dyke, Davis, PLLC

(57) ABSTRACT

Disclosed herein are novel spermine prodrugs and methods of use for treating subjects exhibiting symptoms of a low spermine disorder. Also disclosed are methods of synthesizing spermine prodrugs. Compositions containing spermine prodrugs are also disclosed.

4 Claims, 7 Drawing Sheets

(56) References Cited

OTHER PUBLICATIONS

Murray-Stewart, Tracy et al., "(R,R)-1,12-Dimethylspermine can mitigate abnormal spermidine accumulation in Snyder-Robinson syndrome", J. Biol Chem, 2020, 19 pages.

Nicchitta, Christopher V. et al., "A Regulator of Mitochondrial Calcium Cycling", The Journal of Biological Chemistry, Nov. 10, 1984, vol. 259, No. 21, pp. 12978-12983.

Papot, S. et al., "Design of Selectively Activated Anticancer Prodrugs: Elimination and Cyclization Strategies", Curr. Med Chem.—Anti-Cancer Agents, 2002, vol. 2, pp. 155-185.

Pegg, Anthony E., "The Function of Spermine", International Union of Biochemistry and Molecular Biology, Jan. 2014, vol. 66, No. 1, pp. 8-18.

Rustenbeck, Ingo et al., "Polyamine Modulation of Mitochondrial Calcium Transport", Biochemical Pharmacology, 1998, vol. 56, pp. 987-995.

Salvi, Mauro et al., "Effects of polyamines on mitochondrial Ca2+ transport", Biochimica et Biophysica Acta, 2004, vol. 1661, pp. 113-124.

Simplício, Ana L. et al., "Prodrugs for Amines", Molecules, 2008, vol. 13, pp. 519-547.

Snyder, R.D., MD et al., "Recessive Sex-Linked Mental Retardation in the Absence of Other Recognizable Abnormalties" Clinical Pediatrics, Nov. 1969, vol. 8, No. 11, pp. 669-674.

Schwartz, Charles E. et al., "Synder-Robinson Syndrome" NORD, 2020, https://rarediseases.org/rare-diseases/snyder-robinson-syndrome/ 9 pages.

Soda, Kuniyasu et al., "Long Term Oral Polyamine Intake Increases Blood Polyamine Concentrations", J Nutr Sci Vitaminol, 2009,vol. 55, pp. 361-366.

Til, H.P. et al., "Acute and Subacute Toxicity of Tyramine, Spermidine, Spermine, Putrescine and Cadaverine in Rats", Food and Chemical Toxicology, 1997, vol. 35, pp. 337-348.

Tabor, Celia W. et al., "Pharmacology Of Spermine and Spermidine Some Effects on Animals and Bacteria", Tabor and Rosenthal, 1955, 139-155.

* cited by examiner

SPERMINE PRO-DRUGS

BACKGROUND

Snyder Robinson Syndrome (SRS) was first described by Snyder and Robinson in 1969.[1] In 2003, Cason et al demonstrated that this syndrome resulted from a mutation in the spermine synthase gene (SMS).[2] SMS protein converts spermine (SPM) from its precursor, spermidine (SPD), via the transfer of an aminopropyl group. As shown in FIG. 1, the aminopropyl unit comes from the amino acid methionine after its conversion first to S-adenosylmethionine (SAM) and then to decarboxylated S-adenosylmethionine (dc-SAM) by S-adenosylmethionine decarboxylase (SAMDC).[3] Biochemically, the SMS patients have low levels of intracellular spermine, and elevated spermidine/spermine levels (due to almost no SMS activity). With a low level of SPM, the patients with SRS often battle osteoporosis, scoliosis, facial asymmetry, speech abnormalities, seizures and low bone density.[4-5] This phenotype, in part, may stem from the role of spermine in calcium import[6-10] and other processes.[11] Another phenotype from this X-linked disorder is impaired intellectual function, presumably due to reduced spermine levels in the brain.

Very recently, Casero et al. demonstrated that lymphoblastoid/fibroblast cells derived from SRS patients are capable of transporting exogenous spermine and its analogues (Me₂SPM) into the cell and which result in a significant decrease in the intracellular spermidine pools.[12-13] While our understanding of this disease has led to new diagnostic genetic tools, there are, unfortunately, no therapeutics which cure this ultra-rare disease and physicians are relegated to treating the symptoms. Attempts to treat SRS patients with spermine (the polyamine lacking in these patients) have been unsuccessful.[14] The literature in this area suggests that the administration of spermine (SPM) by intraperitoneal injection or through dietary supplementation led to toxicity or low patient compliance.[15-16]

BRIEF DESCRIPTION OF DRAWINGS

The accompanying drawings, which are incorporated herein and constitute part of this specification, illustrate exemplary embodiments of the invention, and, together with the general description given above and the detailed description given below, serve to explain the features of the invention.

DEFINITIONS

Figure 1:
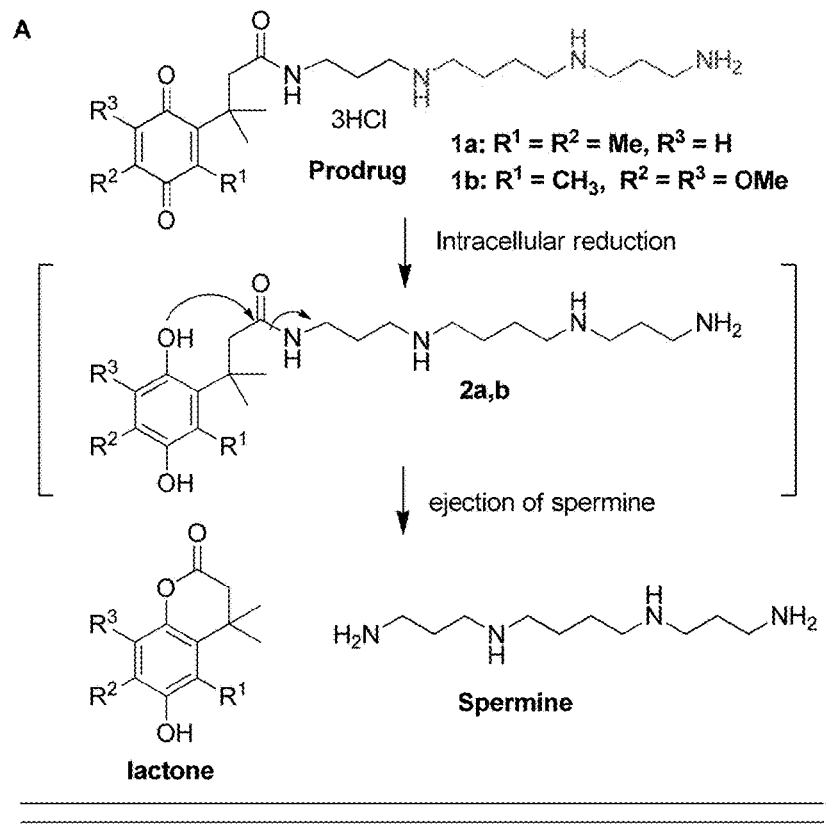
FIG. 1. Panel A, A diagram showing quinone prodrug designs and cyclization chemistry to liberate spermine; Panel B, shows the structures of the native polyamines: putrescine, spermidine, and spermine.
Figure 1:
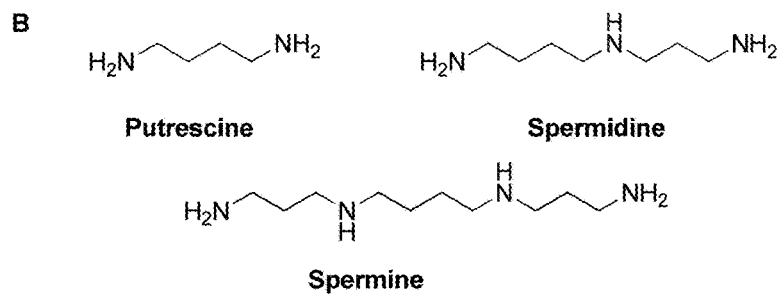

As used herein, the terms "administering" or "administration" of an agent, drug, or peptide to a subject includes any route of introducing or delivering to a subject a compound to perform its intended function. The administering or administration can be carried out by any suitable route, including orally, intranasally, parenterally (intravenously, intramuscularly, intraperitoneally, or subcutaneously), rectally, or topically. Administering or administration includes self-administration and the administration by another.

The term "co-administration" "co-administer(ed)" or "co-administering" as used herein refers to the administration of one agent before, concurrently, or after the administration of another agent such that the biological effects of either agents overlap. The combination of agents as taught herein can act synergistically to treat or prevent the various diseases, disorders or conditions described herein. Using this approach, one may be able to achieve therapeutic efficacy with lower dosages of each agent, thus reducing the potential for adverse side effects.

The term "exemplary therapeutic agent(s)" as used herein refers to a spermine prodrug compound described herein or spermine.

The term "prevent" or "preventions" as used herein means either 1) the reduction in frequency or severity of symptoms commonly associated with a disorder; or 2) a delay or avoidance of additional symptoms associated with the condition or disease, or complete prevention of the disease. One skilled in the art will recognize that wherein the various embodiments are directed to methods of prevention, a subject in need thereof (i.e. a subject in need of prevention) shall include any subject or patient (preferably a mammal, more preferably a human) who has experienced or exhibited at least one symptom of the disorder, disease or condition to be prevented. Further, a subject in need thereof may additionally be a subject (preferably a mammal, more preferably a human) who has not exhibited any symptoms of the disorder, disease or condition to be prevented, but who has been deemed by a physician, clinician or other medical profession to be at risk of developing said disorder, disease or condition. For example, the subject may be deemed at risk of developing a disorder, disease or condition (and therefore in need of prevention or preventive treatment) as a consequence of the subject's medical history, including, but not limited to, family history, pre-disposition, co-existing (co-morbid) disorders or conditions, genetic testing, and the like. In another example, a newborn may not immediately exhibit aspects of the disease at birth but will develop these symptoms over time. In this regard there may exist a time period to prevent the onset of SRS symptoms.

The term "Snyder-Robinson syndrome" or "SRS" as used herein refers to an inherited condition that is characterized by intellectual disability, muscle and bone abnormalities, and other problems with development. Due to this being an X-linked disease, the most profound phenotype typically occurs in males. Symptoms of affected individuals have delayed development that begins in early childhood, speech difficulties, low muscle tone (hypotonia) and muscle mass, difficulty walking and an unsteady gait; thinning of the bones (osteoporosis), an abnormal curvature of the spine (kyphoscoliosis), and unusual facial features including a prominent lower lip, cleft palate, and facial asymmetry. Snyder-Robinson syndrome is caused by mutations in the spermine synthase (SMS) gene and is inherited in an X-linked recessive fashion.

As used herein, the term "subject" refers to any animal (e.g., a mammal), including, but not limited to, humans, non-human primates, rodents, and the like, which is to be the recipient of a particular treatment. We also note that Drosophila (fly) models exist for studying for Snyder Robinson Syndrome (SRS) as well. As such, a subject can also refer to an insect.

A "subject in need" refers to a subject that is diagnosed to be in need of a treatment that involves administration of one or more exemplary therapeutic agents. Typically, a subject in need will exhibit one or more symptoms of SRS.

As used herein "therapeutically effective amount" refers to an amount which, when administered in a proper dosing regimen, is sufficient to reduce or ameliorate the severity, duration, or progression of the disorder being treated, prevent the advancement of the disorder being treated, cause the regression of the disorder being treated, or enhance or improve the prophylactic or therapeutic effect(s) of another therapy. The full therapeutic effect does not necessarily occur by administration of one dose and may occur only after administration of a series of doses. Thus, a therapeutically effective amount may be administered in one or more administrations per day for successive days.

The term "treat" or "treatment" as used herein means administering a compound to manage the symptoms or underlying cause of a condition with the goal of reducing symptoms or signs of the disease and either to prevent or to slow progression, to arrest or potentially to reverse manifestations of the disease, or to inhibit the underlying mechanism(s) causing the disease.

DESCRIPTION

Disclosed herein are new compounds and synthesis methods, wherein the compounds use the special reactivity of the core quinone system to deliver spermine inside cells. Spermine is one of the naturally occurring polyamines and plays important roles in maintaining cell health.[11] In particular, the compounds were tested on Snyder Robinson Syndrome (SRS) cells. It has been found that both spermine and the prodrug 1b successfully delivered spermine to SRS fibroblast cells compared to the wild-type control fibroblasts. Most importantly, both interventions (spermine or 1b) rebalanced intracellular polyamine pools to resemble those found in control fibroblasts. In addition, it was found that the prodrug was effective at doses well below its maximum tolerated dose in vitro. This exciting early discovery provides new hope for a potential therapy for Snyder Robinson Syndrome (SRS).

The approaches disclosed herein rely upon cells recognizing and importing a spermine prodrug (see compounds 1a and 1b; see FIG. 1) into cells via the polyamine transport system. This is possible because they present a 'spermidine message' to the putative cell surface receptor, because one end of the spermine molecule is capped by a latent reactive quinone group (FIG. 1, red color spermidine tail). Once the prodrug is imported into the cell, it encounters the reductive intracellular environment and the quinone is reduced into the respective reactive hydroquinone motif (the respective compound 2a or 2b). This hydroquinone rapidly performs an intramolecular cyclization reaction to liberate free spermine and a stable lactone byproduct (FIG. 1).

Figure 2:
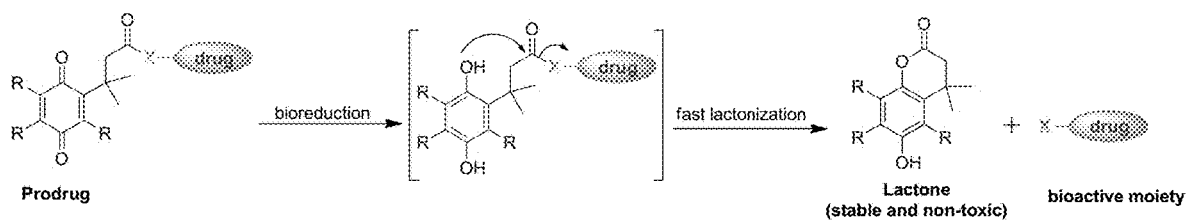
FIG. 2. TLC analysis showing deprotection of prodrug design with a reducing agent. TLC (10% MeOH/1% NH₄OH in CH₂Cl₂) showed the free tri-Boc protected spermine 3 was liberated from the Boc-protected prodrug intermediate 8a, when treated with the reducing agent Na₂S₂O₄. Lane 1: compound 8a, Lane 2: crude reaction mixture of 8a in the presence of aq. Na₂S₂O₄ (shows the loss of 8a and the presence of 3 suggesting that 8a was converted to 3), Lane 3: pure compound 3, Lane 4: a co-spot of Lanes 1-3 showing that the retention factor ($R_f$ value) on the TLC plate is not changed in the presence of the reaction mixture.

Beyond the unique redox abilities of quinone systems, quinones containing a 'trimethyl lock' (TML) motif are found in several prodrug designs due to their intracellular reduction to the reactive hydroquinone form. As shown in FIG. 2, the hydroquinone undergoes a rapid intramolecular lactonization to release an appended bioactive component. The "trimethyl lock" (TML) is a highly versatile molecular release system, which dramatically increases the rate of lactonization of trialkyl-substituted quinone propionic acid derivatives. Due to their special conformational restriction and bio-reductive release, TMLs have been used in modern drug design and cell imaging. The trimethyl lock concept was first described by Carpino et al (Carpino, L. A.; Triolo, S. A.; Berglund, R. A. Reductive lactonization of strategically methylated quinone propionic acid esters and amides. *J Org Chem* 1989, 54, 3303-3310.)

In surveying different amine pro-drug technologies, it was elucidated that the 'trimethyl-lock' quinone-hydroquinone method was very effective and has been used to deliver alcohols and amines.[17] A methyl group at $R^1$ and a large group at $R^2$ have been shown to dramatic increase the rate of ring closure, which facilitates amine release. Moreover, ring mesomeric effects can be used to increase amine release rates by placing electron-donating groups on the aromatic ring in related coumarin systems.[18] In this regard, compound 1b incorporates the best features for optimal delivery and, rewardingly, it works in vitro.

In another embodiment, provided is a chemical synthesis scheme for synthesizing spermine pro-drugs, see Scheme 1 below:

Scheme 1.
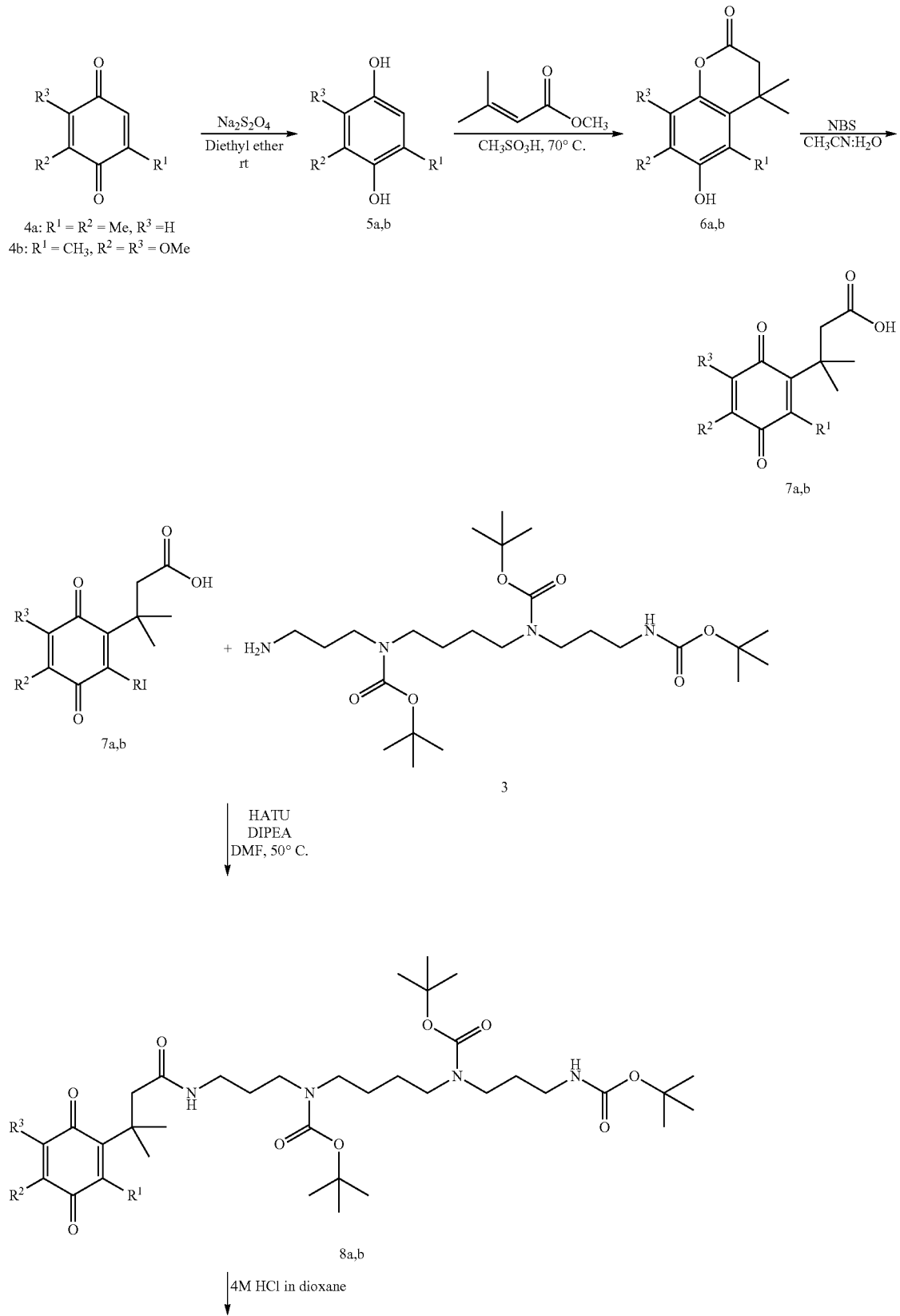

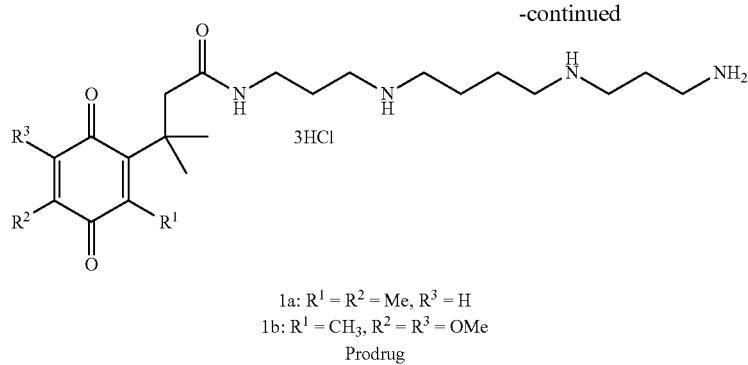

1a: $R^1 = R^2 = Me, R^3 = H$
1b: $R^1 = CH_3, R^2 = R^3 = OMe$
Prodrug

As shown in Scheme 1, two prodrug designs 1a and 1b were synthesized and evaluated for their ability to release spermine in vitro. These synthetic details and compound characterization data are further described in the Examples section herein.

General Chemistry

One skilled in the art will recognize that, where not otherwise specified, any exemplified reaction step(s) may be performed under suitable conditions, according to known methods, to provide the desired product. One skilled in the art will further recognize that, in the specification and claims as presented herein, wherein a reagent or reagent class/type (e.g. base, solvent, etc.) is recited in more than one step of a process, the individual reagents are independently selected for each reaction step and may be the same of different from each other. For example, wherein two steps of a process recite an organic or inorganic base as a reagent, the organic or inorganic base selected for the first step may be the same or different than the organic or inorganic base of the second step. Further, one skilled in the art will recognize that wherein a reaction step of various embodiments may be carried out in a variety of solvents or solvent systems, said reaction step may also be carried out in a mixture of the suitable solvents or solvent systems.

Examples of suitable solvents, bases, reaction temperatures, and other reaction parameters and components are provided in the detailed description which follows herein. One skilled in the art will recognize that the listing of specific examples is not intended, and should not be construed, as limiting in any way the various embodiments set forth in the claims which follow thereafter.

To provide a more concise description, some of the quantitative expressions given herein are not qualified with the term "about". It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value.

To provide a more concise description, some of the quantitative expressions herein are recited as a range from about amount X to about amount Y. It is understood that wherein a range is recited, the range is not limited to the recited upper and lower bounds, but rather includes the full range from about amount X through about amount Y, or any range therein.

For use in medicine, the salts of the exemplary therapeutic agents refer to non-toxic "pharmaceutically acceptable salts." Other salts may, however, be useful in the preparation of compounds according to various embodiments or of their pharmaceutically acceptable salts. Suitable pharmaceutically acceptable salts of the compounds include acid addition salts which may, for example, be formed by mixing a solution of the amine containing compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid, phosphoric acid or linear alkanoic acids like caproic acid to form a salt. Furthermore, where the compounds of various embodiments carry an acidic moiety (like in compound 7 in Scheme 1), suitable acceptable salts thereof may include alkali metal salts, e.g., sodium or potassium salts; alkaline earth metal salts, e.g., calcium or magnesium salts; and salts formed with suitable organic ligands, e.g., quaternary ammonium salts or the free acid form may be preferred for long term storage of this synthetic intermediate. Thus, for the prodrug designs representative pharmaceutically acceptable salts include, but are not limited to, the following: acetate, benzenesulfonate, benzoate, bicarbonate, bisulfate, bitartrate, borate, bromide, calcium edetate, camsylate, caprate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide, and valerate.

Representative acids which may be used in the preparation of pharmaceutically acceptable salts of the prodrug include, but are not limited to, the following: acids including acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, (+)-camphoric acid, camphorsulfonic acid, (+)-(1S)-camphor-10-sulfonic acid, capric acid, caproic acid, caprylic acid, cinnamic acid, citric acid, cyclamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucoronic acid, L-glutamic acid, α-oxoglutaric acid, glycolic acid, hipuric acid, hydrobromic acid, hydrochloric acid, (+)-L-lactic acid, (±)-DL-lactic acid, lactobionic acid, maleic acid, (−)-L-malic acid, malonic acid, (±)-DL-mandelic acid, methanesulfonic acid, naphthalene- 2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, phosphoric acid, L-pyroglutamic acid, salicylic acid, 4-amino-salicylic acid, sebaic acid, stearic acid, succinic acid, sulfuric acid, tannic acid, (+)-L-tartaric acid, thiocyanic acid, p-toluenesulfonic acid, and undecylenic acid.

Various embodiments may include spermine prodrugs. As used herein, the term "prodrug" refers to a biologically inactive compound that can be metabolized in the body to produce a drug. In general, such prodrugs may be functional derivatives of the compounds which are readily convertible in vivo into the required compound. Thus, in the methods of treatment of various embodiments, the term "administering" shall encompass the treatment of the various disorders described with the compound specifically disclosed or with a compound which may not be specifically disclosed, but which converts to the specified compound in vivo after administration to the patient. Conventional procedures for the selection and preparation of suitable prodrug derivatives are well-known to those of ordinary skill in the art.

Pharmaceutical Compositions, Dosing and Therapeutic Methods

The exemplary therapeutic agents according to various embodiments are useful in the treatment of disorders that involve low levels of spermine, such as SRS. Various embodiments may, therefore, provide a method of treating disorders associated with low spermine levels comprising administering to a subject in need thereof a therapeutically effective amount of one or more exemplary therapeutic agents. To those skilled in the art a similar reactive TML quinone approach could be used to create putrescine and spermidine prodrugs to deliver putrescine or spermidine for treating disorders associated with low putrescine or spermidine levels. In this regard, the invention describes a general method to deliver polyamines to cells via a quinone prodrug design.

In an optional embodiment, methods involve administering one or more exemplary therapeutic agents and co-administering one or more adjunctive agents. Examples of adjunctive agents include antioxidants and amine oxidase inhibitors. Examples of antioxidants include, but are not limited to, curcumin, resveratrol (3,5,4'-trans-trihydroxystilbene), quercetin, 3,3,4,5,7-penta-hydroxyflavone, silymarin, milk thistle or Saint Mary's thistle, naringenin is also recognized as 5,7,4'-thihydroxyflavanone, (–)-epigallocatechin-3-gallate (EGCG), alpha lipoic acid, lycopene (LYC) is an acyclic isomer of beta-carotene, N-acetylcysteine, and vitamin C (Ascorbic acid). Examples of amine oxidase inhibitors include, but are not limited to, aminoguanidine, N1-Methyl-N2-(2,3-butadienyl)-1,4-butanediamine (MDL 72521), N1,N2-bis(2,3-butadienyl)-1,4-butanediamine (MDL 72527), chlorhexidine, PXS-4728A, methoctramine. 1,8-diaminooctane, 1,12-diaminododecane, N-prenylagmatine (G3), and guazatine.

According to various embodiments, an exemplary therapeutic agent or adjunctive agent may be administered in a therapeutically effective amount in the range of from about 0.01 mg/kg of body weight to about 20 mg/kg of body weight, or any amount or range therein. For example, an exemplary therapeutic agent may be administered in a therapeutically effective amount in the range having a lower limit and/or an upper limit. The range can include or exclude the lower limit and/or the upper limit. The lower limit and/or upper limit can be selected from about 0.01, 0.5, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, and 20 mg/kg of body weight. For example, according to certain embodiments, an exemplary therapeutic agent may be administered in a therapeutically effective amount in the range of from about 1 mg/kg of body weight to about 15 mg/kg of body weight, or any combination of lower limits and upper limits described.

Various embodiments may further comprise pharmaceutical compositions containing one or more exemplary therapeutic agents with a pharmaceutically acceptable carrier. Pharmaceutical compositions containing one or more of the compounds according to various embodiments as the active ingredient can be prepared by intimately mixing the compound or compounds with a pharmaceutical carrier according to conventional pharmaceutical compounding techniques. The carrier may take a wide variety of forms depending upon the desired route of administration (e.g., oral, parenteral). Thus, for liquid oral preparations such as suspensions, elixirs and solutions, suitable carriers and additives include water, glycols, oils, alcohols, flavoring agents, preservatives, stabilizers, coloring agents and the like; for solid oral preparations, such as powders, capsules and tablets, suitable carriers and additives include starches, sugars, diluents, granulating agents, lubricants, binders, disintegrating agents and the like. Solid oral preparations may also be coated with substances such as sugars or be enteric-coated so as to modulate major site of absorption. For parenteral administration, the carrier will usually consist of sterile water and other ingredients may be added to increase solubility or preservation. Injectable suspensions or solutions may also be prepared utilizing aqueous carriers along with appropriate additives.

Furthermore, compositions may be provided that include at least one exemplary therapeutic agent combined with at least one adjunctive agent. Examples of adjunctive agents include antioxidants and amine oxidase inhibitors. Examples of antioxidants include, but are not limited to, curcumin, resveratrol (3,5,4'-trans-trihydroxystilbene), quercetin, 3,3,4,5,7-penta-hydroxyflavone, silymarin, milk thistle or Saint Mary's thistle, naringenin is also recognized as 5,7,4'-thihydroxyflavanone, (–)-epigallocatechin-3-gallate (EGCG), alpha lipoic acid, lycopene (LYC) is an acyclic isomer of beta-carotene, N-acetylcysteine, and vitamin C (Ascorbic acid). Examples of amine oxidase inhibitors include, but are not limited to, aminoguanidine, N1-Methyl-N2-(2,3-butadienyl)-1,4-butanediamine (MDL 72521), N1,N2-bis(2,3-butadienyl)-1,4-butanediamine (MDL 72527), chlorhexidine, PXS-4728A, methoctramine. 1,8-diaminooctane, 1,12-diaminododecane, N-prenylagmatine (G3), and guazatine.

To prepare the pharmaceutical compositions according to various embodiments, one or more compounds may be intimately admixed with a pharmaceutical carrier according to conventional pharmaceutical compounding techniques, which carrier may take a wide variety of forms depending on the form of preparation desired for administration, e.g., oral or parenteral such as intramuscular. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents, and the like; for solid oral preparations such as, for example, powders, capsules, caplets, gelcaps and tablets, suitable carriers and additives include starches, sugars, diluents, granulating agents, lubricants, binders, disintegrating agents, and the like. Because of their ease in administration, tablets and capsules represent the most advantageous oral dosage unit form, in which case solid pharmaceutical carriers are obviously employed. If desired, tablets may be sugar-coated or enteric-coated by standard techniques. For parenterals, the carrier will usually comprise sterile water, through other ingredients, for example, for purposes such as aiding solubility or for preservation, may be included. Injectable suspensions may also be prepared, in which case appropriate liquid carriers, suspending agents and the like may be employed. The pharmaceutical compositions herein will contain, per dosage unit, e.g., tablet, capsule, powder, injection, teaspoonful and the like, an amount of the active ingredient necessary to deliver an effective dose as described above. The pharmaceutical compositions according to various embodiments may contain an active ingredient in an amount, per unit dosage unit, e.g., tablet, capsule, powder, injection, suppository, teaspoonful and the like, of from about 0.01 to about 1500 mg or any amount or range therein. For example, the pharmaceutical compositions according to various embodiments may contain an active ingredient in an amount, per unit dosage unit, e.g., tablet, capsule, powder, injection, suppository, teaspoonful and the like, within a range having a lower limit and/or an upper limit. The range may include or exclude the lower limit and/or the upper limit. The lower limit and/or upper limit can be selected from about 0.01, 0.5, 1, 5, 10, 20, 30, 40, 50, 60, 70, 80, 90, 100, 200, 300, 400, 500, 600, 700, 800, 900, 1000, 1100, 1200, 1300, 1400, 1500, 1600, 1700, 1800, 1900, and 2000 mg. For example, according to certain embodiments, the pharmaceutical compositions according to various embodiments may contain an active ingredient in an amount, per unit dosage unit, e.g., tablet, capsule, powder, injection, suppository, teaspoonful and the like, of from about 0.01 to about 1500 mg, or any combination of lower limits and upper limits described.

Furthermore, the pharmaceutical compositions according to various embodiments may be administered at a dosage of from about 0.01 to about 100 mg/kg/day, or any amount or range therein, preferably from about 0.01 to about 20 mg/kg/day, or any amount or range therein. The dosages, however, may be varied depending upon the requirement of the patients, the severity of the condition being treated, and the compound being employed. The use of either daily administration or post-periodic dosing may be employed. For example, the pharmaceutical compositions according to various embodiments may be administered at a dosage within a range having a lower limit and/or an upper limit. The range may include or exclude the lower limit and/or the upper limit. The lower limit and/or upper limit can be selected from about 0.01, 0.5, 1, 5, 10, 20, 30, 40, 50, 60, 70, 80, 90, 100, 110, 120, 130, 140, 150, 160, 170, 180, 190, and 200 mg/kg/day. For example, according to certain embodiments, the pharmaceutical compositions according to various embodiments may be administered at a dosage of from about 0.5 to about 50 mg/kg/day, or any combination of lower limits and upper limits described.

Preferably these compositions are in unit dosage forms from such as tablets, pills, capsules, powders, granules, sterile parenteral solutions or suspensions, metered aerosol or liquid sprays, drops, ampoules, autoinjector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound according to various embodiments, or a pharmaceutically acceptable salt thereof. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from about 0.01 to about 1000 mg of the active ingredient of various embodiments, or any amount or range therein. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

The liquid forms in which the novel compositions of various embodiments may be incorporated for administration orally or by injection include, aqueous solutions, suitably flavored syrups, aqueous or oil suspensions, and flavored emulsions with edible oils such as cottonseed oil, sesame oil, coconut oil or peanut oil, as well as elixirs, and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone, or gelatin.

The method of treating low spermine disorders or diseases described in various embodiments may also be carried out using a pharmaceutical composition comprising any of the compounds as defined herein and a pharmaceutically acceptable carrier. The pharmaceutical composition may contain between about 0.01 mg and 1000 mg of the compound, or any amount or range therein; preferably about 0.5 to 500 mg of the compound, or any amount or range therein, and may be constituted into any form suitable for the mode of administration selected. Carriers include necessary and inert pharmaceutical excipients, including, but not limited to, binders, suspending agents, lubricants, flavorants, sweeteners, preservatives, dyes, and coatings. Compositions suitable for oral administration include solid forms, such as pills, tablets, caplets, capsules (each including immediate release, timed release and sustained release formulations), granules, and powders, and liquid forms, such as solutions, syrups, elixers, emulsions, and suspensions. Forms useful for parenteral administration include sterile solutions, emulsions and suspensions.

Advantageously, compounds according to various embodiments may be administered in a single daily dose, or the total daily dosage may be administered in divided doses of two, three or four times daily. Furthermore, compounds according to various embodiments can be administered in intranasal form via topical use of suitable intranasal vehicles, or via transdermal skin patches well known to those of ordinary skill in that art. To be administered in the form of a transdermal delivery system, the dosage administration will, of course, be continuous rather than intermittent throughout the dosage regimen.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders, lubricants, disintegrating agents, and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride, and the like. Disintegrators include, without limitation, starch, methyl cellulose, agar, bentonite, xanthan gum and the like.

The liquid forms in suitably flavored suspending or dispersing agents such as the synthetic and natural gums, for example, tragacanth, acacia, methyl-cellulose and the like. For parenteral administration, sterile suspensions and solutions are desired. Isotonic preparations which generally contain suitable preservatives are employed when intravenous administration is desired.

To prepare a pharmaceutical composition according to various embodiments, a compound of formula (I) as the active ingredient is intimately admixed with a pharmaceutical carrier according to conventional pharmaceutical compounding techniques, which carrier may take a wide variety of forms depending of the form of preparation desired for administration (e.g. oral or parenteral). Suitable pharmaceutically acceptable carriers are well known in the art. Those having ordinary skill in the art will be well-apprised of various pharmaceutically acceptable carriers.

Exemplary therapeutic agents according to various embodiments may be administered in any of the foregoing compositions and according to dosage regimens established in the art whenever treatment of low spermine related disorders is required.

The daily dosage of the products may be varied over a wide range from about 0.01 to about 1,500 mg per adult human per day, or any amount or range therein. For oral administration, the compositions are preferably provided in the form of tablets containing, 0.01, 0.05, 0.1, 0.5, 1.0, 2.5, 5.0, 10.0, 15.0, 25.0, 50.0, 100, 150, 200, 250 and 500 milligrams of the active ingredient for the symptomatic adjustment of the dosage to the patient to be treated. An effective amount of the drug is ordinarily supplied at a dosage level of from about 0.01 mg/kg to about 100 mg/kg of body weight per day, or any amount or range therein. Preferably, the range is from about 0.01 to about 50.0 mg/kg of body weight per day, or any amount or range therein. More preferably, from about 0.01 to about 20.0 mg/kg of body weight per day, or any amount or range therein. The compounds may be administered on a regimen of 1 to 4 times per day.

Optimal dosages to be administered may be readily determined by those skilled in the art, and will vary with the particular compound used, the mode of administration, the strength of the preparation, the mode of administration, and the advancement of the disease condition. In addition, factors associated with the particular patient being treated, including patient age, weight, diet, and time of administration, will result in the need to adjust dosages.

One skilled in the art will recognize that, both in vivo and in vitro trials using suitable, known and generally accepted cell and/or animal models are predictive of the ability of a test compound to treat or prevent a given disorder. One skilled in the art will further recognize that human clinical trials including first-in-human, dose ranging and efficacy trials, in healthy patients and/or those suffering from a given disorder, may be completed according to methods well known in the clinical and medical arts. The determination of a therapeutically effective dose of the exemplary therapeutic agents is well within the capability of those skilled in the art. A therapeutically effective dose refers to that amount of active ingredient which increases intracellular spermine compared to that which occurs in the absence of the therapeutically effective dose. Therapeutic efficacy and toxicity, e.g., ED50 (the dose therapeutically effective in 50% of the population) and LD50 (the dose lethal to 50% of the population), can be determined by standard pharmaceutical procedures in cell cultures or experimental animals. The dose ratio of toxic to therapeutic effects is the therapeutic index, and it can be expressed as the ratio, LD50/ED50.

The exact dosage will be determined by the practitioner, in light of factors related to the subject that requires treatment. Dosage and administration are adjusted to provide sufficient levels of the active ingredient or to maintain the desired effect. Factors which can be taken into account include the severity of the disease state, activity of the defective SMS protein, general health of the subject, age, weight, and gender of the subject, diet, time and frequency of administration, drug combination(s), reaction sensitivities, and tolerance/response to therapy. Long-acting compositions can be administered every 3 to 4 days, every week, or once every two weeks depending on the half-life and clearance rate of the particular formulation.

Normal dosage amounts can vary from 0.1 to 100,000 micrograms, up to a total dose of about 1 g, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc. In typical embodiments, exemplary therapeutic agents according to various embodiments may increase intracellular spermine by at least about 10-100 percent.

EXAMPLES

Example 1: Synthesis of Prodrugs 1a and 1b

These were synthesized by similar methods. For example, to an ice cold solution of compound 8b (0.2 mmol) in DCM (1 mL) was added 4M HCl in dioxane (1 mL). The resulting reaction mixture was allowed to stir at room temperature for 45 min. The solvent was then evaporated to dryness to provide a light brown solid. Diethyl ether (5 mL) was added to the obtained solid and sonicated for 2 min. The solvent was then decanted and the remaining solid was dried under reduced pressure to give the hydrochloride salt of 1b as a light brown, highly hygroscopic solid.

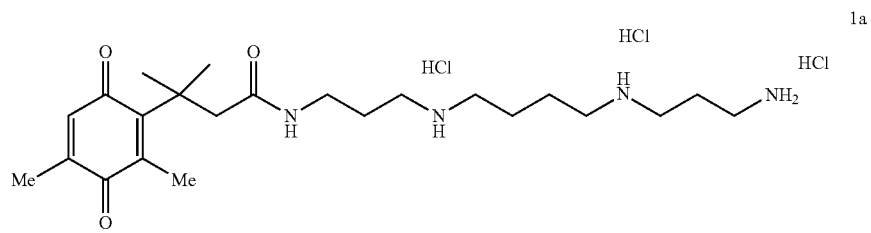 [SMILES: Cl ; CC1=CC(=O)C(C(C)(C)CC(=O)NCCCNCCCCNCCCN)=C(C)C1=O ; Cl ; Cl]

1a

1a: Light brown very hydroscopic solid, yield 61%, $^1$H NMR (400 MHz, D$_2$O) δ 6.74 (s, 1H), 3.60 (dq, 6H), 3.12 (m, 14H), 2.16 (m, 12H), 1.78 (m, 7H), 1.60 (m, 5H), 1.17 (m, 9H).

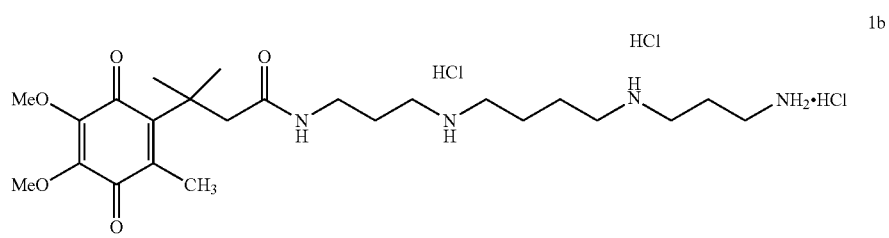

1b

1b: Light brown solid, yield 85%, $^1$H NMR (500 MHz, d$_6$-DMSO) δ 9.29-9.22 (m, 4H), 8.12 (s, 4H), 3.92 (s, 3H), 3.88 (s, 3H), 2.97-2.92 (m, 6H), 2.83 (s, 6H), 2.05-1.90 (m, 6H), 1.67-1.64 (m, 6H), 1.11 (s, 3H), 0.91 (s, 3H); $^{13}$C NMR (125 MHz, D$_2$O) δ 196.7, 196.2, 192.5, 177.0, 149.5, 149.2, 61.4, 61.2, 48.0, 47.0, 44.5, 44.0, 42.1, 36.5, 24.8, 23.7, 22.7, 22.4, 16.3; Anal. Chem. for C$_{24}$H$_{45}$Cl$_3$N$_4$O$_5$.1H$_2$O; theory: C, 47.10, H, 7.74, N, 9.15; found: C, 47.33, H, 7.59, N, 9.13.

Quinone starting materials 4a and 4b (Scheme 1) were purchased from Sigma Aldrich and used without further purification.

Example 2: Synthesis of Hydroquinone 3

In general, to a solution of the respective quinone 4 (Scheme 1, 5.4 mmol) in diethyl ether (25 mL) was added a solution of Na$_2$S$_2$O$_4$ (16.2 mmol) in water (25 mL).[19] The resulting reaction mixture was stirred at room temperature for 1 h. After consuming the starting material, water was added (15 mL) and extracted using diethyl ether (2×50 mL). The combined diethyl ether layer was dried over anhydrous sodium sulfate, filtered and concentrated to dryness to give pure hydroquinone 5 (Scheme 1) in 66-90% yields.

Colorless solid[19], yield 66%, R$_f$=0.4 (20% EtOAc: Hexanes).

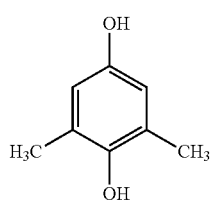

5a

Colorless solid, yield 90%, $^1$H NMR (500 MHz, CDCl$_3$) δ 6.49 (d, J=0.7 Hz, 1H), 5.39 (s, 1H), 5.27 (s, 1H), 3.91 (s, 3H), 3.88 (s, 3H), 2.17 (d, J=0.7 Hz, 3H); $^{13}$C NMR (125 MHz, CDCl$_3$) δ 141.6, 140.4, 139.1, 137.2, 119.4, 111.3, 60.8, 60.7, 15.4.

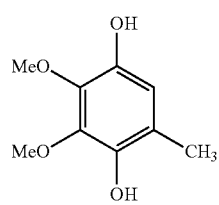

5b

Example 3: Synthesis of Lactone 6 (Scheme 1)

To a mixture of the respective hydroquinone 5 (Scheme 1; 5.4 mmol) and methyl 3,3-dimethylacrylate (7.0 mmol) was added methanesulfonic acid (10 mL).[20] The resulting reaction mixture was stirred at 70° C. for 90 min. Upon completion of the reaction, the contents were cooled to room temperature. Cold water (50 mL) was added and the mixture extracted using ethyl acetate (2×30 mL). The combined organic layer was washed with saturated sodium bicarbonate solution (30 mL), dried over anhydrous sodium sulfate, filtered and concentrated under reduced pressure to give the crude product. The obtained crude product was recrystallized from 10% ethylacetate:hexanes to produce the pure lactone 6 in 67-72% yields as colorless solid.

Colorless solid, yield 67%, $^1$H NMR (400 MHz, CDCl$_3$) δ 1.45 (s, 6H), 2.23 (s, 3H), 2.37 (s 3H), 2.56 (s, 2H), 4.76 (s, 1H), 6.71 (s, 1H); $^{13}$C NMR (100 MHz, CDCl$_3$) δ 169.1, 149.6, 145.1, 128.9, 123.1, 122.5, 117.1, H$_3$C CH$_3$ 46.4, 35.7, 28.1, 16.2, 14.8.

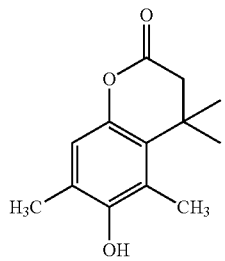

6a

Colorless solid, yield 72%, $^1$H NMR (400 MHz, CDCl$_3$) δ 5.76 (s, 1H), 3.97 (s, 3H), 3.90 (s, 3H), 2.57 (s, 2H), 2.33 (s, 3H), 1.45 (s, 6H); $^{13}$C NMR (125 MHz, CDCl$_3$) δ 167.7, 143.9, 138.6, 138.4, 138.3, 126.4, 116.4, 61.5, 61.2, 45.9, 35.8, 27.7, 13.7

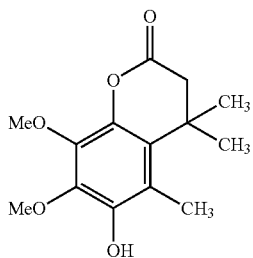

6b

Example 4: Synthesis of Sodium Salt 7a (Scheme 1)

To a solution of lactone 6a (3.1 mmol) in acetonitrile (100 mL) was added N-bromosuccinimide (NBS) solution (3.1 mmol) at room temperature.[4] The reaction mixture was stirred at the same temperature for 1 h. After consuming the starting material as indicated by TLC, water (20 mL) was added and extracted using diethyl ether (3×25 mL). The resulting crude was dried over anhydrous sodium sulfate, filtered, and concentrated under reduced pressure to give the crude product (476 mg, 2 mmol). The crude was then dissolved in acetonitrile (50 mL) and basified (pH 10) using a 5% NaHCO$_3$ solution (41 mL) and stirred overnight. After conversion of the crude to the sodium salt, as observed by TLC (5% MeOH in DCM), the reaction was concentrated to dryness to yield the sodium salt 7a. Colorless solid, yield 19%, $^1$H NMR (400 MHz, D$_2$O) δ 6.46 (d, J=1.3 Hz, 1H), 2.64 (s, 2H), 2.00 (s, 3H), 1.85 (d, J=1.1 Hz, 3H), 1.28 (s, 6H).

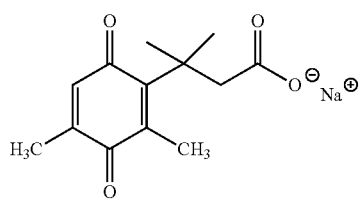

7a

Example 5: Synthesis of Acid 7b (Scheme 1)

Similarly, to a solution of lactone 6b (0.75 mmol) in acetonitrile (10 mL) was added N-bromosuccinimide (NBS) solution (1.5 mmol, 10% aqueous acetonitrile) at room temperature.[20] The reaction mixture was stirred at the same temperature for 1 h. After consuming the starting material, as indicated by TLC, water (20 mL) was added and extracted using diethyl ether (2×25 mL). The combined organic layer was washed with saturated NaHCO$_3$ solution (20 mL). The aqueous layer was acidified to pH 2 using 1N HCl and extracted using diethyl ether (3×25 mL). The combined organic layer was dried over anhydrous sodium sulfate, filtered, and evaporated to dryness to give acid 7b in 25% yield as a yellow oil. We observed that the obtained acid was unstable, when exposed to light and air.

Yellow oil, yield 25%, $^1$H NMR (500 MHz, CDCl$_3$) δ 3.97 (s, 3H), 3.90 (s, 3H), 3.06 (s, 2H), 2.15 (s, 3H), 1.46 (s, 6H); $^{13}$C NMR (125 MHz, CDCl$_3$) δ 186.4, 184.5, 177.7, 149.8, 145.3, 142.4, 137.7, 60.9, 60.4, 47.1, 38.2, 28.9, 14.0.

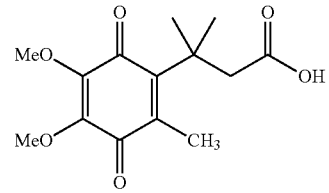

7b

Example 6: Synthesis of Amide 8 (Scheme 1)

In general, each acid was coupled to the Boc-protected spermine motif 3. For example, to a solution of acid 7 (0.12 mmol) in DMF (1 mL) was added HATU (0.36 mmol) and diisopropylethylamine (DIPEA, 0.36 mmol) at room temperature. The resulting reaction mixture was stirred at 50° C. for 15 min. Next, a solution of tri-Boc-spermine 3 (0.13 mmol in 0.2 mL DMF) was added and the solution stirred overnight. After the starting materials were consumed (as indicated by TLC), the mixture was cooled to room temperature, water (10 mL) added and the product extracted using ethyl acetate (2×10 mL). The combined organic layer was washed with saturated aqueous NaHCO$_3$ (10 mL), followed by 1N HCl (10 mL), the

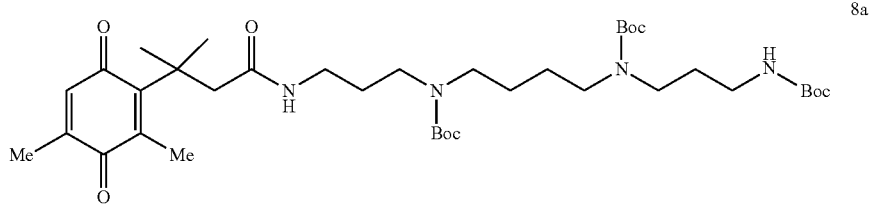 [SMILES: CC1=CC(=O)C(C(C)(C)CC(=O)NCCCN(CCCCN(CCCNC(=O)OC(C)(C)C)C(=O)OC(C)(C)C)C(=O)OC(C)(C)C)=C(C)C1=O]

organic layer was separated, dried over anhydrous Na₂SO₄, filtered, and concentrated to give the crude product. The obtained crude product was purified through column chromatography using ethyl acetate:hexanes as eluent to provide each of the pure respective amides 8 in 60-70% yields as a light orange oil.

8a: Light orange oil, yield 70%, $^1$H NMR (400 MHz, CDCl$_3$) δ 6.75 (s, 1H), 3.17 (m, 14H), 2.87 (m, 2H), 2.12 (m, 8H), 1.51 (s, 6H), 1.45 (m, 27H) 1.46 (m, 4H), 1.45 (s, 3H), 0.90 (s, 3H); $^{13}$C NMR (100 MHz, CDCl$_3$) δ (196.8, 194.5, 174.0, 155.7, 155.3, 151.5, 137.3, 82.4, 79.0, 78.9, 77.3, 77.0, 76.7, 53.2, 49.9, 46.2, 40.9, 39.8, 30.5, 29.6, 28.1, 25.6, 22.4, 15.7, 9.8; Anal. Calcd for C$_{38}$H$_{64}$N$_4$O$_9$·0.5 H$_2$O: C, 61.76; H, 8.87; N, 7.58. Found: C, 61.86; H, 8.73, N, 7.86.

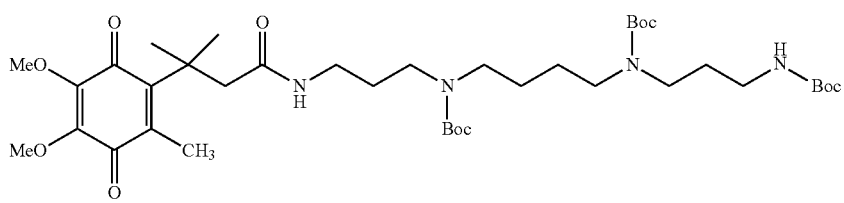

8b: Light orange oil, yield 70%, $^1$H NMR (500 MHz, CDCl$_3$) δ 3.89 (s, 3H), 3.86 (s, 3H), 3.17 (s, 4H), 3.04 (s, 8H), 2.79 (s, 2H), 2.73 (s, 3H), 1.39 (s, 18H), 1.37 (s, 9H), 1.35 (s, 8H), 1.18 (s, 6H); $^{13}$C NMR (125 MHz, CDCl$_3$) δ 186.4, 184.6, 171.8, 165.8, 156.5, 156.1, 151.9, 146.4, 141.9, 135.3, 79.9, 79.8, 79.6, 60.7, 60.2, 56.0, 49.3, 46.7, 43.2, 38.7, 38.2, 35.3, 29.7, 28.6, 28.5, 27.8, 14.2, 13.8.

Example 7: Biological Evaluation

Figure 3:
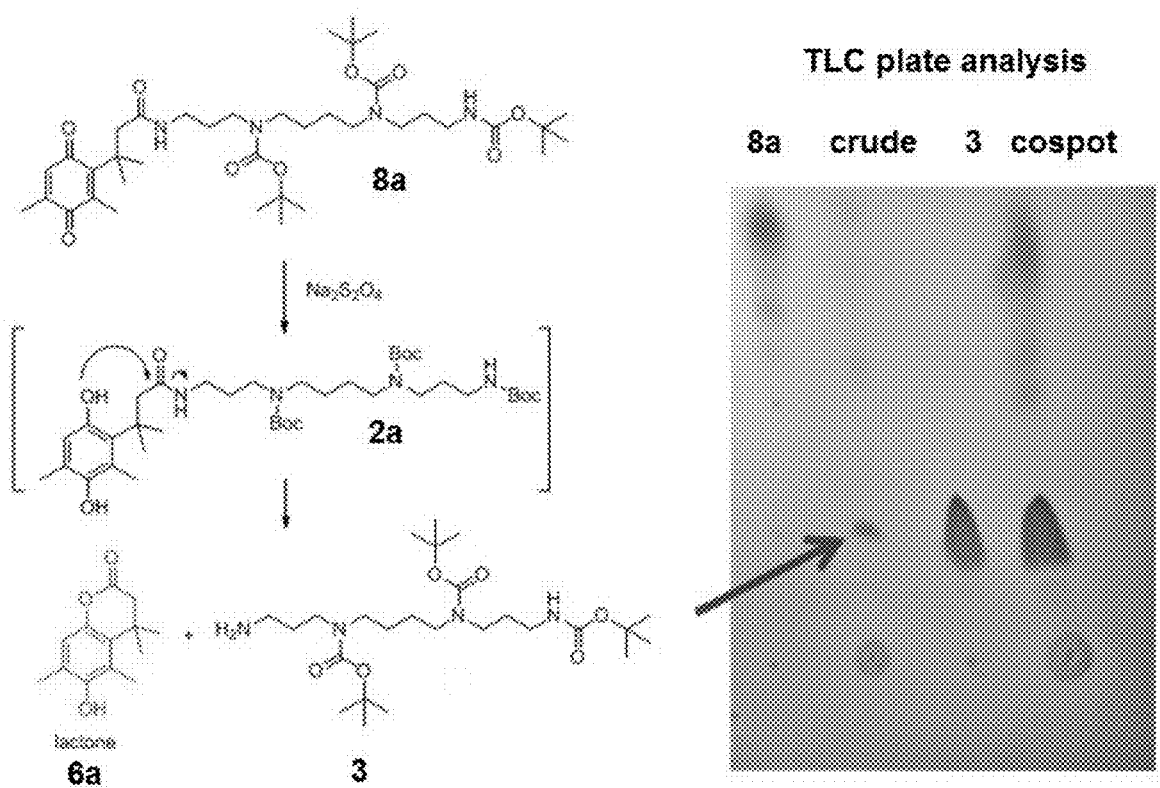
FIG. 3. A diagram showing the principle of the molecular release of the 'trimethyl lock' quinone systems FIG. 4. Naturally occurring redox of coenzyme Q10 to ubiquinol and the structure of 1b (in box).

The quinone motif in 1a was first tested for its ability to unmask and eject an adjacent amine motif. To demonstrate that the methylated quinone design in 1a would react under reducing conditions, we attempted to de-protect 8a using a reducing agent. The Boc-protected compound 8a was placed in the presence and absence of the reducing agent sodium dithionite (Na₂S₂O₄) and analyzed by thin layer chromatography (TLC). As shown in FIG. 3, in the presence of the inorganic reductant (Na₂S₂O₄), tri-Boc-spermine 3 was released and appears at the correct R$_f$ for the authentic tri-Boc-spermine (3) on the thin layer chromatography (TLC) plate.

The prodrug 1a was tested in cell culture using an 'induced SRS scenario' in L3.6pl pancreatic cancer cells using the known spermine synthase inhibitor, cyclohexyl-1,3-diaminopropane (CDAP). Prior work demonstrated that 100 µM CDAP was not toxic to L3.6pl cells after 72 h incubation at 37° C., but had a profound effect on the intracellular polyamine levels, with a severe 95% decrease in spermine levels.[21] It was then demonstrated that CDAP (100 µM), the prodrug 1a (10 µM) and spermine (1 µM) were not toxic to these cells under the conditions of the experiment (72 h). Exogenous spermine (1 µM) or the prodrug 1a (at 1 or 10 µM) were tested to determine whether they could rebalance the polyamine pools of these cells as measured by HPLC analysis of washed L3.6pl cell lysates.

As shown in Table 1, neither the prodrug 1a nor spermine significantly increased the intracellular spermine pools in these cells under these conditions of SMS inhibition.

TABLE 1

Polyamine levels in L3.6pl pancreatic cancer cells in the presence and absence of the SMS inhibitor CDAP.

| Experiment | Putrescine (nmol/mg protein) | Spermidine (nmol/mg protein) | Spermine (nmol/mg protein) |
| --- | --- | --- | --- |
| Untreated control | 12.1 ± 3.3 | 35.6 ± 13.4 | 15.2 ± 6.5 |
| CDAP (100 µM) | 1.9 ± 0.7 | 53.4 ± 6.2 | 0.8 ± 0.1 |
| CDAP (100 µM) + Spermine (1µM) | 3.8 ± 2.1 | 69.4 ± 11.0 | 1.3 ± 0.2 |
| CDAP (100 uM) + prodrug 1a (1 µM) | 3.2 ± 0.3 | 65.7 ± 4.5 | 1.1 ± 0.2 |
| CDAP (100 uM) + prodrug 1a (10 µM) | 3.3 ± 1.2 | 63.9 ± 18.5 | 1.2 ± 0.3 |

FIG. 3 clearly showed that if the quinone was reduced, it would liberate the attached amine motif. However, the data in Table 1 suggested that the prodrug was not releasing spermine inside L3.6pl cells. This implied that the methylated quinone motif in 1a may not be reduced in vitro to produce significant amounts of spermine. It was speculated that lack of reactivity of 1a might be responsible for failure to generate spermine inside cells and that this outcome might have to do with the reduction potential of the methylated quinone in 1a.

Figure 4:
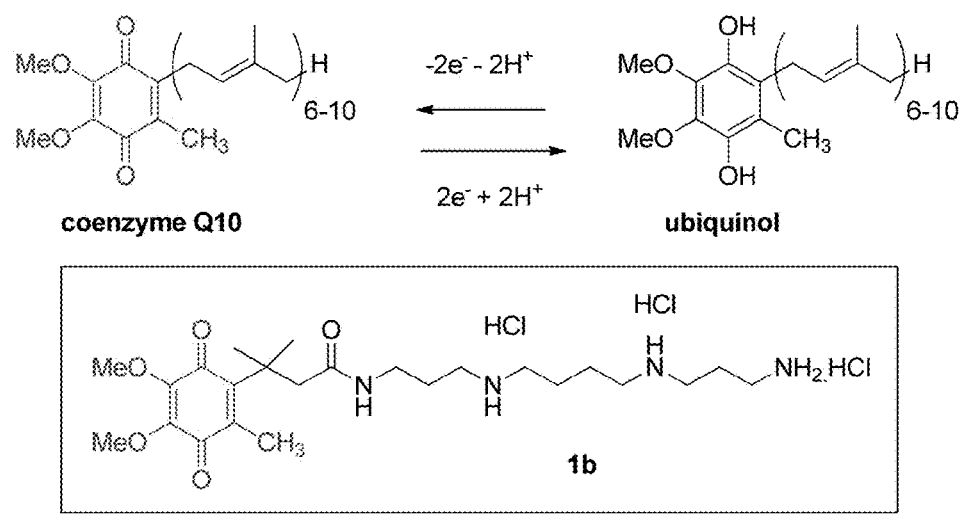

To address this presumed lack-of-reactivity issue, prodrug 1b was synthesized. This dimethoxy-quinone motif in 1b resembles the naturally occurring ubiquinone (coenzyme Q) and is readily reduced inside cells (see FIG. 4). The methoxy groups facilitate the quinone reduction. The synthesis of prodrug 1b is shown in Scheme 1 and is made by a similar approach to 1a.

Armed with a more reactive prodrug design 1b, its toxicity and ability to replenish spermine levels in SRS cells was evaluated. Spermine was also tested and a recent paper suggested that spermine itself could enter and rebalance polyamine pools in SRS lymphoblast cell lines.[22] Since SRS lymphoblasts had already been studied, these studies focused on the SRS fibroblast cell lines.

The toxicity of the polyamine biosynthesis inhibitor DFMO and compound 1b and spermine in SRS and control fibroblast cells (CMS-24949 and CMS-26559) was tested. As shown in Table 2, these cells were relatively insensitive to DFMO and had very high $IC_{50}$ values (Table 2). As shown in Table 3, spermine, prodrug 1b, and lactone 6b were all non-toxic to cells at the highest dose tested (100 µM).

TABLE 2

72 h $IC_{50}$ values (mM) for DFMO in wild type and SRS fibroblast cells

| Entry | Cells | DFMO $IC_{50}$ (mM) |
|---|---|---|
| 1 | CMS-24949 (wild type) | >27.7 |
| 2 | CMS-26559 (SMS-mutant) | 17.1 |

TABLE 3

72 h Toxicity Evaluation of Spermine, prodrug 1b, and lactone 6b in CMS-24949 (wild type) and CMS-26559 (SMS-mutant) fibroblast cells

| Entry | Compound | $IC_{50}$ (µM) | MTD (µM) |
|---|---|---|---|
| 1 | Spermine | >100 | >100 |
| 2 | Prodrug 1b | >100 | >100 |
| 3 | Lactone 6b | >100 | >100 |

Figure 5:
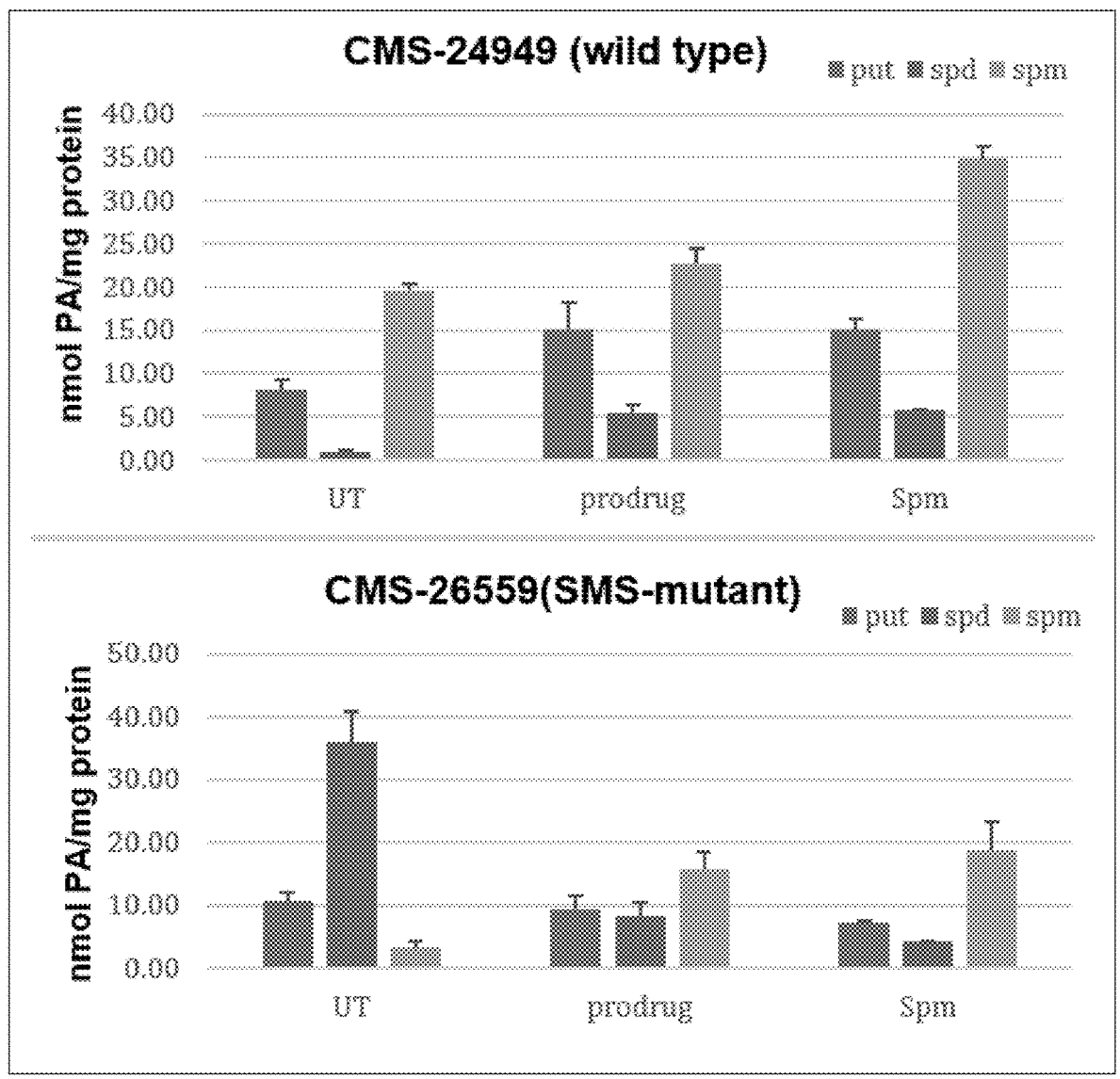
FIG. 5. Rebalancing of polyamine pools (expressed in nmol/mg protein) in SRS fibroblasts compared to wild type fibroblasts. Either the prodrug 1b or exogenous spermine at 5 μM in the presence of 250 μM aminoguanidine (AG, an amine oxidase inhibitor) was able to enter and rebalance polyamine pools (as measured by the N-dansylation HPLC protocol) after 72 h at 37° C. The prodrug resulted in a five-fold increase in intracellular spermine pools in the SMS mutant consistent with successful delivery as planned. Legend: UT=untreated, prodrug=compound 1b, Spm=spermine, color codes: Put=putrescine, spd=spermidine, spm=spermine
Figure 6:
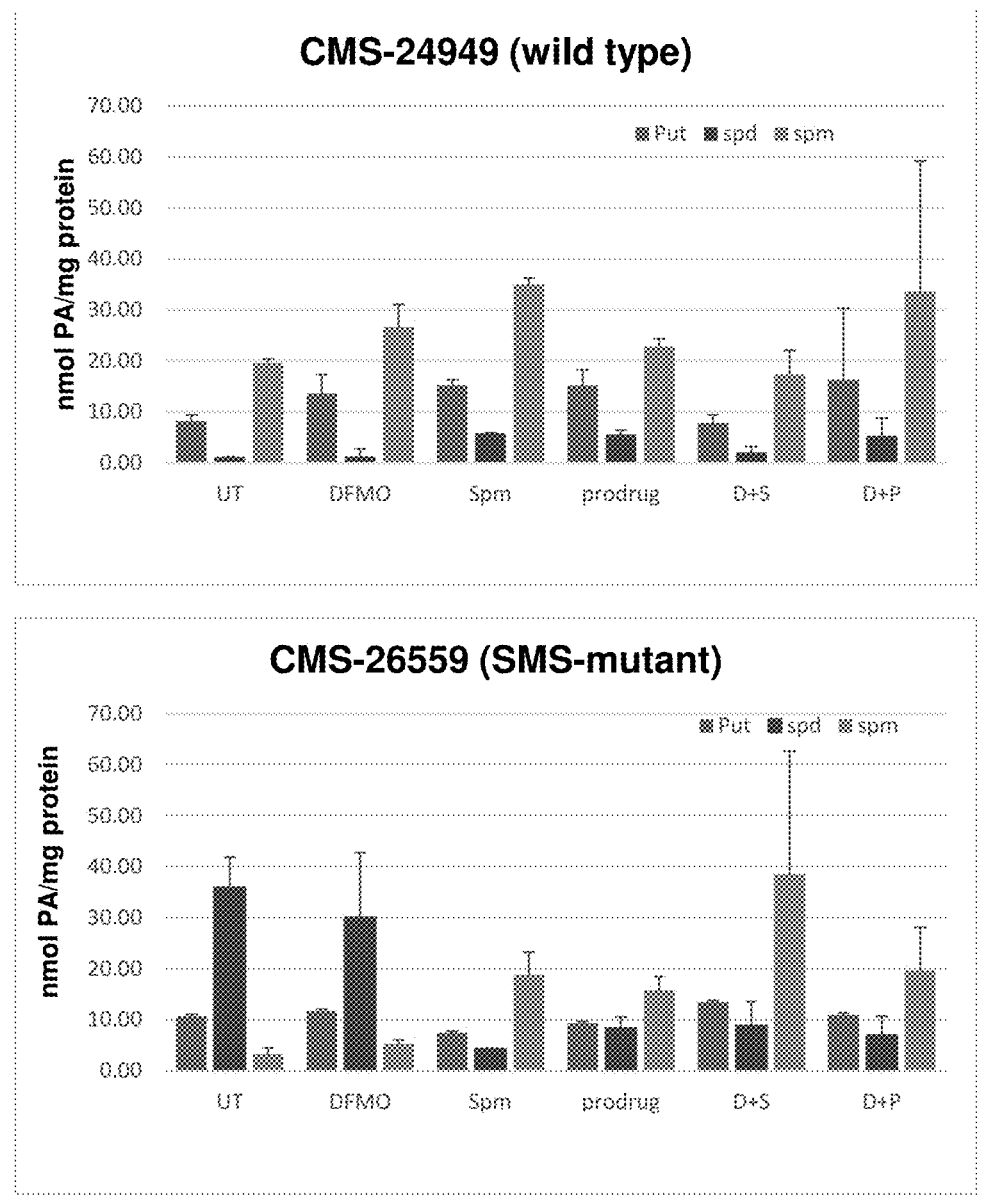
FIG. 6: HPLC polyamine levels (expressed in nmol/mg protein) in the presence of spermine or prodrug 1b treatments in the presence of DFMO (27.7 mM for wild type, 17.1 mM for mutant cells) and AG (250 μM) in SRS (SMS mutant) fibroblasts compared to wild type fibroblasts. Legend: UT=untreated, DFMO=difluoromethylornithine, Spm=spermine, prodrug=compound 1b, D+S=DFMO+Spm, D+P=DFMO+prodrug 1b; color codes: Put=putrescine, spd=spermidine, spm=spermine FIG. 7. Stability studies of prodrug 1b in the presence and absence of AG (250 μM) in complete DMEM media containing 15% fetal bovine serum and Pen/Strep antibiotic cocktail.

The cells were dosed and evaluated to determine how much spermine was present inside the cells (i.e. successfully delivered) in the presence and absence of each compound (spermine vs prodrug 1b). Successful spermine delivery would appear as increased spermine levels inside the cell by HPLC analysis. As shown in FIG. 5, significant increases in intracellular spermine levels in the presence of either exogenous spermine or prodrug 1b at 5 µM was observed. This was also tried with and without DFMO addition to see if 'triggering' obligate polyamine transport (via DFMO addition and inhibition of polyamine biosynthesis) would increase uptake of these two polyamine-containing compounds into cells. As shown in FIG. 6, the increase in intracellular spermine levels was essentially independent of DFMO addition suggesting that basal polyamine uptake was sufficient to take up exogenous spermine or prodrug 1b.

Snyder Robinson Syndrome fibroblast cell lines were received from the Greenwood Genetic Center (GGC). The wild type (CMS-24949) and mutant (CMS-26559) cells were grown in Dulbecco's Modified Eagle Medium (DMEM) supplemented with 15% fetal bovine serum (FBS), 1% penicillin/streptomycin and 1% glutamine in in a humidified 5% $CO_2$ atmosphere at 37° C. For uptake experiment, the wild type ($0.25 \times 10^6$ cells per 10 cm dish) and mutant ($0.65 \times 10^6$ cells per 10 cm dish) were grown in the presence of 250 µM aminoguanidine (AG) to inhibit extracellular oxidation of spermine by bovine serum amine oxidase present in the culture medium. The fibroblast cells CMS-24949 (wild type) and CMS-26559 (SMS-mutant) were incubated in the presence of exogenous spermine (Spm) or prodrug 1b alone or in combination with the ODC inhibitor DFMO to determine if basal or obligate polyamine uptake/transport was required to deliver spermine or prodrug 1b in SRS fibroblast cells. Specifically, the mutant and wild type cells were incubated with 250 µM AG and six different conditions such as untreated (UT), DFMO (the 72 h $IC_{50}$ value 17.1 mM for the mutant or the max DFMO dose tested 27.7 mM for the wild type), Spm (5 µM), prodrug 1b (5 µM), combination of DFMO+Spm (D+S) and DFMO+prodrug 1b (D+P) for 72 h and the results are depicted in FIGS. 5 and 6. The presence of DFMO did not drastically alter the rescue effect (FIG. 6).

Regardless of condition, the intracellular polyamine levels (putrescine (Put), spermidine (Spd), and spermine (Spm); structures in FIG. 1 Panel B) were not significantly changed in the wild type cells CMS-24949 and the relative pattern was similar to control (FIG. 5). Surprisingly, these wild type fibroblast cells were very insensitive to DFMO even at the very high dose of DFMO (27.7 mM). Due to the high levels of DFMO needed to affect growth of these wt cells, the IC50 dose of DFMO in this wild type cell line was not determined and we simply used the high dose of 27.2 mM to see what effect, if any a high dose of DFMO would have on the polyamine pools. In sum, DFMO did not have much of an effect on changing spermine pools when co-dosed with spermine or prodrug 1b (FIG. 6).

As shown in FIG. 5, as expected, the basal spermine level was found to be very low in the untreated SMS-mutant cells and the spermidine (Spd) level was very high. Treatment of SMS-mutant cells (CMS-26559) with the ODC inhibitor (DFMO) at its $IC_{50}$ concentration (17.1 mM) significantly reduced putrescine levels and increased the intracellular Spd and Spm levels. Interestingly, treatment with either exogenous Spm or prodrug 1b only at 5 µM dramatically increased the intracellular Spm level and decreased the Spd level. The same trend was observed in the presence of DFMO+Spm and DFMO+prodrug 1b suggesting that basal and not obligate transport was sufficient to replenish polyamine pools in SRS fibroblasts. This experiment suggests that the basal polyamine transport system was active, and the SRS fibroblast cells could rebalance their polyamine pools in presence of either exogenous spermine or our synthesized prodrug 1b in a similar manner. The Spd/Spm ratios of the SRS lines decreased from their baseline (untreated) values 11.12 to 0.23 for Spm and 0.52 for prodrug 1b treatment (FIG. 5).

One interesting finding was that the high 'commitment' of wild type fibroblast cells to spermine as evidenced by the high intracellular spermine levels compared to spermidine in the untreated wild type fibroblasts. In sharp contrast, the mutant SMS fibroblasts had very low spermine (as expected) and had high intracellular spermidine levels. Interestingly, the wild type fibroblasts were insensitive to DFMO (even to very high doses like 27.7 mM) and were seemingly unchanged by most of our interventions. In contrast, the intracellular levels of polyamines were rebalanced in the mutant SMS fibroblasts in the presence of exogenous spermine or our prodrug 1b. It was observed that these mutant SMS fibroblast cells were also more sensitive to DFMO (72 h $IC_{50}$ 17.1 mM) than wild type fibroblasts. These results show that a therapeutic intervention is possible by harnessing polyamine transport to replenish depleted spermine pools.

Figure 7:
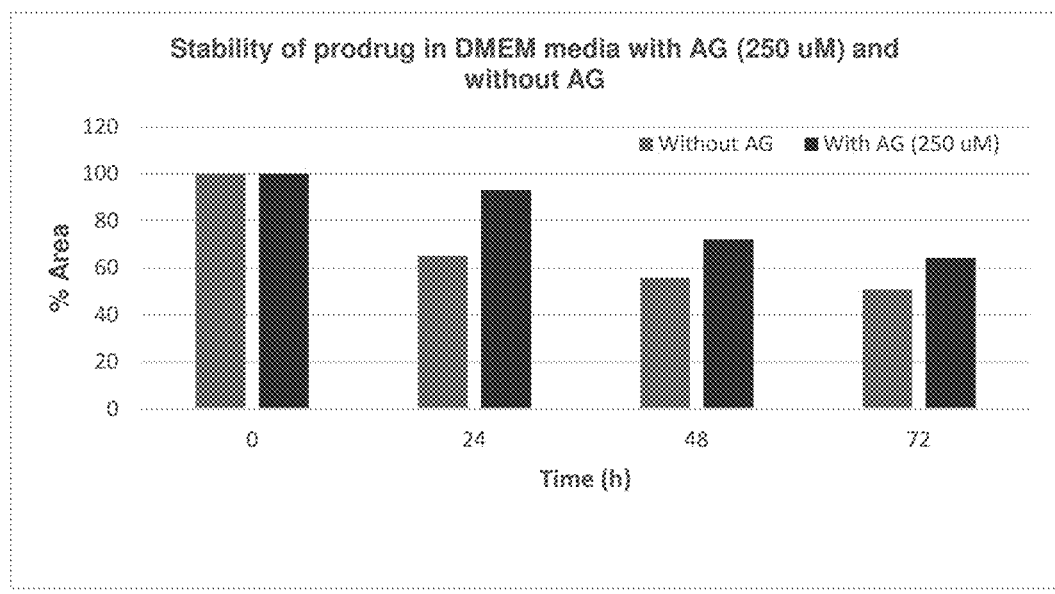

A priori, prodrug 1b contains a free aminopropyl 'tail' and was thus expected to be a substrate for amine oxidases present in the culture media.[23] As such, one would expect to see a slower rate of degradation in the presence of the amine oxidase inhibitor AG. As shown in FIG. 7, the rate of decomposition of the prodrug was, indeed, slower in the presence of AG, which directly supports amine oxidases as being a major degradation pathway for this prodrug compound in culture. After 24 h, there was 93% prodrug 1b remaining in the presence of AG (250 µM), but only 65% remaining in the absence of AG. The estimated half-life of prodrug 1b in the absence of AG was 72 h (where 50% of the prodrug still remained intact). In the presence of 250 µM AG, 64% of the prodrug remained intact after 72 h suggesting that one could increase the level of AG to better protect the prodrug over longer term experiments >24 h. These experiments suggested that addition of an amine oxidase inhibitor like AG would be beneficial to a prodrug 1b or spermine based therapy by slowing down or inhibiting the degradation of the polyamine motifs present in these amine-containing substances.

Sample Preparation and Derivatization[24]:

The biological samples (~2 million cells washed 3× with ice cold PBS and then harvested by trypsinization) were homogenized using a hypersonic needle for 5 sec (typically three times) in presence of 150 µL of 0.2 M perchloric acid buffer ($HClO_4$/1M NaCl) and 50 µL of 0.9% aqueous NaCl solution. The obtained milky solution was then centrifuged at 5000 rpm for 10 min to give clear supernatant layer. The total volume of supernatant layer was measured by pipette and recorded for each sample. The remaining cell pellet was saved and used for protein level determination using the Bicinchoninic Acid (BCA) method. Each supernatant (100 µL) was transferred to a 4 mL glass vial, and two internal standards, α-methyl-phenylalanine (10 µL, 2 mM in 2% PCA solution) and 1,7-heptanediamine (10 µL, 400 µm in 2% PCA solution), were added and resulting mixture was vortexed for 30 sec. Next, an aqueous carbonate buffer (pH 9.5, 240 µL) was added to each vial followed by freshly prepared dansyl chloride solution (400 µL) in dry acetone (20 mg/mL) addition. All vials were then capped, vortexed for good mixing, and incubated at 60° C. in rotary shaker for 60 min. After this incubation, 25 µL of L-alanine (100 mg/mL in water) was added to quench the remaining dansyl chloride in each vial and the incubation was continued for an additional 15 min. The solvent was evaporated to dryness using a rotary evaporator to give a colorless solid residue. The residue was then dissolved in water (300 µL) and chloroform (1.0 mL) was added to this water solution and the mixture was vortexed for 30 sec. The reaction mixture was then centrifuged at 1000 rpm for 4 min to obtain a clean layer separation. The bottom chloroform layer (containing the dansyl polyamines) and top water layer (containing the amino acids) were each transferred separately into different vials. The chloroform layer was evaporated to dryness under reduced pressure give a residue. To this residue, methanol (1.0 mL) was added and vortexed to dissolve the dansylated polyamines. The methanol solution (containing the dansylated polyamines) was passed through a C18 plug and additional methanol (0.5 mL) was passed through the plug to generate approximately 1.5 mL of a filtered methanol solution containing the dansylated polyamines. The water layer (containing amino acids) was acidified using 1M HCl solution (300 µL) to pH 3 and methanol (0.9 mL) was added to this mixture. The mixture was filtered through a 0.45 µm nylon syringe filter (to remove any particles) into another vial. To analyze the polyamines and amino acid together in the same HPLC run, we mixed the chloroform-derived and water-derived methanol solutions equally by volume (0.75 mL each, total of 1.5 mL volume in the HPLC vial) and the solution (80 µL) then injected into the HPLC for analysis.

HPLC Conditions:

A 0-40% gradient of mobile phase A [100% acetonitrile (ACN)] and B [25 mM sodium acetate buffer (pH 5.94) containing 3% 1-propanol, and 10% ACN] was run for 40 min at 1 mL $min^{-1}$ to elute all N-dansylated amino acids. In order to elute the dansylated polyamines within the same run, the gradient was then raised from 40% to 100% ACN in 15 min at a flow rate of 2.5 mL $min^{-1}$.

Other Considerations.

Since spermine alone was effective in rebalancing the spermine content in SRS cells, a diet rich in spermine (e.g., natto) may also provide a potential therapy.[25] Indeed, the toxicity of oral spermine is known to be 19 mg spermine/kg body weight/day.[26] However, high doses of spermine (475 mg/kg/day, 5000 ppm) were shown to have adverse effects in rats including emaciation, aggressiveness, convulsions, and paralysis of the hind legs.[26] The toxicity is thought to occur via the oxidation of spermine by amine oxidases to form reactive aldehydes and reactive oxygen species. Interestingly, this issue can be overcome by the addition of aminoguanidine, a known amine oxidase inhibitor. Indeed, the spermine rescue experiments shown here were conducted in the presence of 250 µM aminoguanidine to suppress the degradation of spermine in cell culture. The success of this approach of using a combination therapy of spermine with an amine oxidase inhibitor (like aminoguanidine) to rebalance polyamine pools and increase spermine in SRS cells suggests that a therapy containing spermine and aminoguanidine could also be used to treat SRS patients. The same benefit of AG can be applied to the prodrug 1b, where more remained over time. There are other known inhibitors of polyamine oxidase that could also benefit this approach including N1-Methyl-N2-(2,3-butadienyl)-1,4-butanediamine (MDL 72521) and N1,N2-bis(2,3-butadienyl)-1,4-butanediamine (MDL 72527) are specific, potent, enzyme-activated, irreversible inhibitors of polyamine oxidase in vitro.[27] In addition, chlorhexidine and methoctramine have been shown to inhibit polyamine oxidase.[28, 29]

Figure 8:
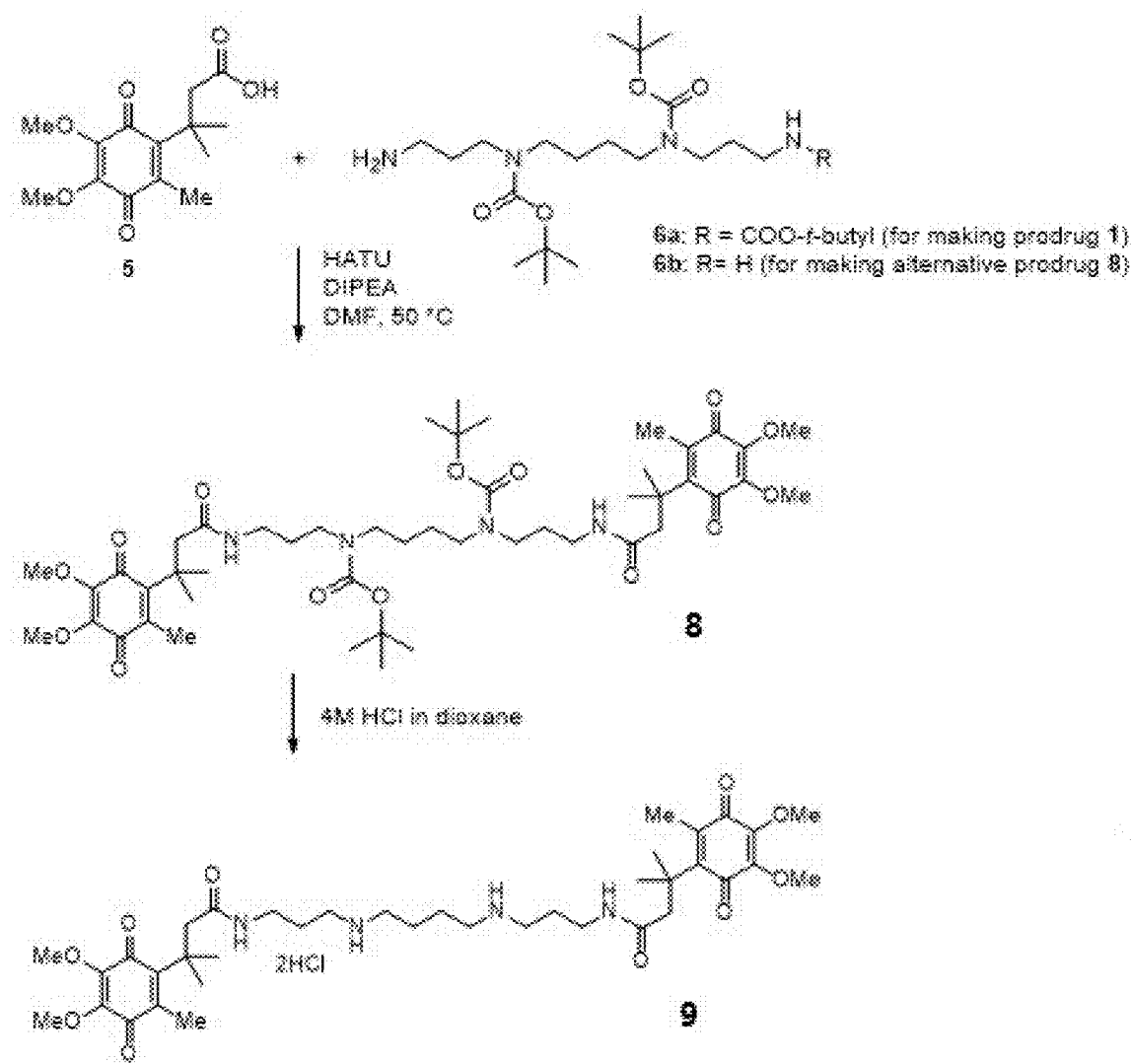
FIG. 8. Synthesis of di-substituted system, prodrug 9

Another approach is the synthesis of a prodrug 9 (FIG. 8) where both ends of the spermine molecule are capped with the TML quinone substituent present in 1a or 1b. This di-substituted design illustrated in FIG. 8 caps both free terminal amine groups of spermine and should protect the prodrug from degradation by amine oxidases.

Summary.

Figure 9:
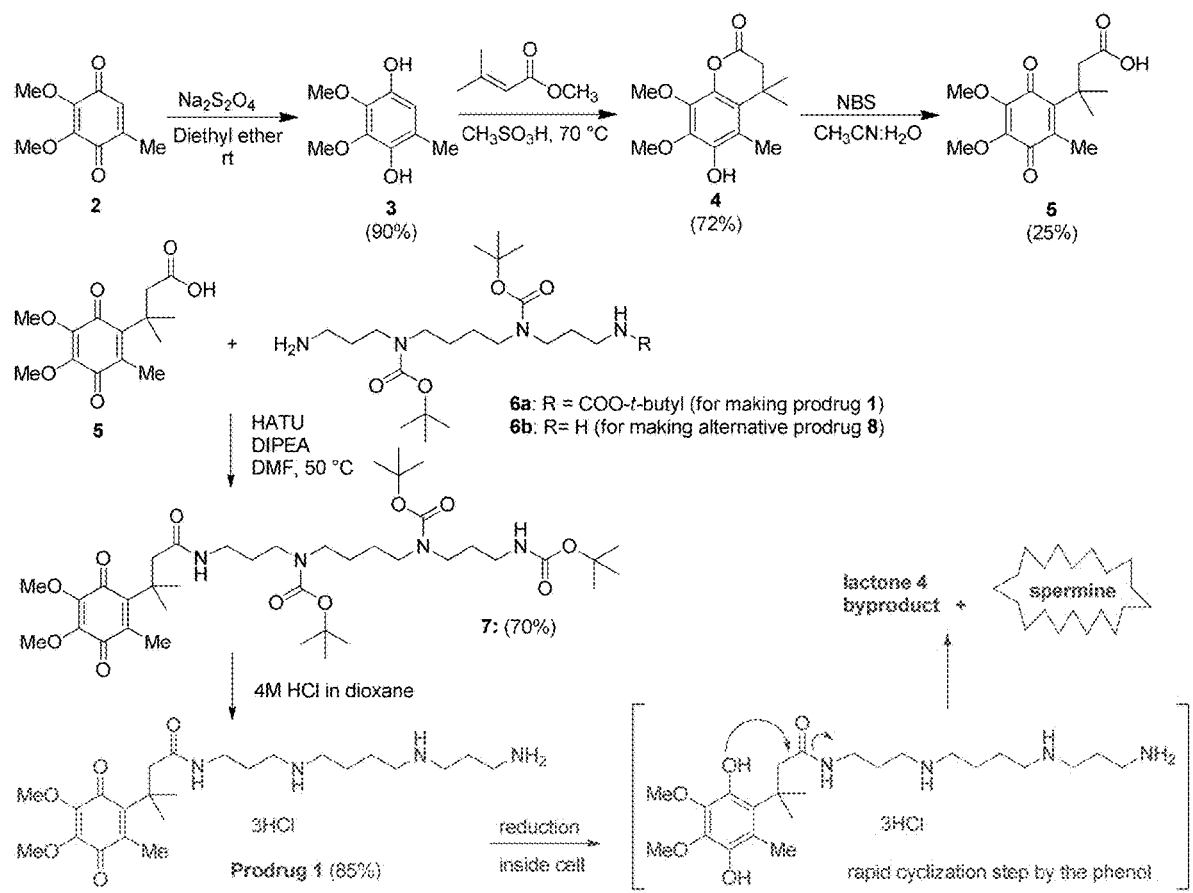
FIG. 9. Prodrug 1b synthesis and spermine release after bio-reduction of prodrug 1b (red)

As demonstrated in the Examples and related data, a pro-drug for spermine was successfully developed, which releases spermine inside cells and rebalances the spermidine/spermine ratios inside SRS cells closer to those observed in wild-type fibroblasts. It has also been shown that spermine by itself can also be taken up by these cells in the presence of an amine oxidase inhibitor like aminoguanidine and can be used to rebalance the intracellular polyamine pools. Importantly, the prodrug is effective at concentrations well below its maximum tolerated concentration (MTC) in vitro. FIG. 9 shows the scheme of synthesizing prodrug 1b and the reduction in cells to produce spermine and a lactone byproduct. We note that the Boc-protected prodrugs (e.g., 7 in FIG. 9) may also liberate spermine under the right conditions of high acidity (low pH encountered after oral uptake in the gastric acid of the stomach) and a reductive cell environment. In this regard, the precursors themselves (e.g. 7 in FIG. 9 or 2 in FIG. 3) may be prodrugs of spermine as well.

Having described the many embodiments of the disclosed invention in detail, it will be apparent that modifications and variations are possible without departing from the scope of the invention defined in the appended claims. Furthermore, it should be appreciated that all examples in the present disclosure, while illustrating many embodiments of the invention, are provided as non-limiting examples and are, therefore, not to be taken as limiting the various aspects so illustrated.

It is intended that the invention not be limited to the particular embodiment disclosed herein contemplated for carrying out this invention, but that the invention will include all embodiments falling within the scope of the claims.

The teachings of references cited herein are incorporated herein in their entirety to the extend not inconsistent with the present disclosure and embodiments.

REFERENCES

1. Snyder, R. D.; Robinson, A., Recessive sex-linked mental retardation in the absence of other recognizable abnormalities. Report of a family. *Clin Pediatr* (Phila) 1969, 8 (11), 669-674.
2. Cason, A. L.; Ikeguchi, Y.; Skinner, C.; Wood, T. C.; Holden, K. R.; Lubs, H. A.; Martinez, F.; Simensen, R. J.; Stevenson, R. E.; Pegg, A. E.; Schwartz, C. E., X-linked spermine synthase gene (SMS) defect: the first polyamine deficiency syndrome. *Eur J Hum Genet* 2003, 11 (12), 937-944.
3. Ikeguchi, Y.; Bewley, M. C.; Pegg, A. E., Aminopropyltransferases: Function, Structure and Genetics. *J. Biochem* 2006, 139 (1), 1-9.
4. Albert, J. S.; Bhattacharyya, N.; Wolfe, L. A.; Bone, W. P.; Maduro, V.; Accardi, J.; Adams, D. R.; Schwartz, C. E.; Norris, J.; Wood, T.; Gafni, R. I.; Collins, M. T.; Tosi, L. L.; Markello, T. C.; Gahl, W. A.; Boerkoel, C. F., Impaired osteoblast and osteoclast function characterize the osteoporosis of Snyder-Robinson syndrome. *Orphanet J Rare Dis* 2015, 10, 27.
5. de Alencastro, G.; McCloskey, D. E.; Kliemann, S. E.; Maranduba, C.; Pegg, A. E.; Wang, X.; Bertola, D. R.; Schwartz, C. E.; Passos-Bueno, M. R.; Sertie, A. L., New SMS mutation leads to a striking reduction in spermine synthase protein function and a severe form of Snyder-Robinson X-linked recessive mental retardation syndrome. *Journal of medical genetics* 2008, 45 (8), 539-543.
6. Jensen, J. R.; Lynch, G.; Baudry, M., Polyamines stimulate mitochondrial calcium transport in rat brain. *J Neurochem* 1987, 48 (3), 765-772.
7. Nicchitta, C. V.; Williamson, J. R., Spermine. A regulator of mitochondrial calcium cycling. *J Biol Chem* 1984, 259 (21), 12978-12983.
8. Rustenbeck, I.; Eggers, G.; Reiter, H.; Munster, W.; Lenzen, S., Polyamine modulation of mitochondrial calcium transport. I. Stimulatory and inhibitory effects of aliphatic polyamines, aminoglucosides and other polyamine analogues on mitochondrial calcium uptake. *Biochem Pharmacol* 1998, 56 (8), 977-985.
9. Rustenbeck, I.; Loptien, D.; Fricke, K.; Lenzen, S.; Reiter, H., Polyamine modulation of mitochondrial calcium transport. II. Inhibition of mitochondrial permeability transition by aliphatic polyamines but not by aminoglucosides. *Biochem Pharmacol* 1998, 56 (8), 987-995.
10. Salvi, M.; Toninello, A., Effects of polyamines on mitochondrial Ca(2+) transport. *Biochim Biophys Acta* 2004, 1661 (2), 113-124.
11. Pegg, A. E., The function of spermine. *IUBMB Life* 2014, 66 (1), 8-18.
12. Stewart, T. M.; Khomutov, M.; Foley, J. R.; Guo, X.; Holbert, C. E.; Dunston, T. T.; Schwartz, C. E.; Gabrielson, K.; Khomutov, A.; Casero, R. A., (R, R)-1, 12-Dimethylspermine can mitigate abnormal spermidine accumulation in Snyder-Robinson syndrome. *Journal of Biological Chemistry* 2020, 295 (10), 3247-3256.
13. Murray-Stewart, T.; Dunworth, M.; Foley, J. R.; Schwartz, C. E.; Casero, R. A., Polyamine homeostasis in Snyder-Robinson syndrome. *Medical sciences* 2018, 6 (4), 112.
14. Syndrome, S. R., https://rarediseases.org/rare-diseases/snyder-robinson-syndrome/.
15. Tabor, C. W.; Rosenthal, S. M., Pharmacology of spermine and spermidine. Some effects on animals and bacteria. *Journal of Pharmacology and Experimental Therapeutics* 1956, 116 (2), 139-155.
16. Wang, X.; Levic, S.; Gratton, M. A.; Doyle, K. J.; Yamoah, E. N.; Pegg, A. E., Spermine Synthase Deficiency Leads to Deafness and a Profound Sensitivity to α-Difluoromethylornithine. *Journal of Biological Chemistry* 2009, 284 (2), 930-937.
17. Papot, S.; Tranoy, I.; Tillequin, F.; Florent, J. C.; Gesson, J. P., Design of selectively activated anticancer prodrugs: elimination and cyclization strategies. *Curr Med Chem Anticancer Agents* 2002, 2 (2), 155-185.
18. Simplicio, A. L.; Clancy, J. M.; Gilmer, J. F., Prodrugs for amines. *Molecules* 2008, 13 (3), 519-547.
19. Johnson-Ajinwo, O. R.; Li, W.-W., Stable isotope dilution gas chromatography-mass spectrometry for quantification of thymoquinone in black cumin seed oil. *J. Agric. Food Chem.* 2014, 62 (24), 5466-5471.
20. Carpino, L. A.; Triolo, S. A.; Berglund, R. A., Reductive lactonization of strategically methylated quinone propionic acid esters and amides. *J. Org. Chem* 1989, 54 (14), 3303-3310.
21. Massaro, C.; Thomas, J.; Phanstiel, O., Investigation of Polyamine Metabolism and Homeostasis in Pancreatic Cancers. *Med. Sci.* 2017, 5 (32), doi:10.3390/medsci5040032.
22. Murray-Stewart, T.; Dunworth, M.; Foley, J. R.; Schwartz, C. E.; Casero, R. A., Jr., Polyamine Homeostasis in Snyder-Robinson Syndrome. *Med Sci* (Basel) 2018, 6 (4), 112.
23. Agostinelli, E.; Arancia, G.; Vedova, L. D.; Belli, F.; Marra, M.; Salvi, M.; Toninello, A., The biological functions of polyamine oxidation products by amine oxidases: perspectives of clinical applications. *Amino Acids* 2004, 27 (3-4), 347-58.
24. Minocha, S. C.; Minocha, R.; Robie, C. A., High-Performance Liquid-Chromatographic Method for the Determination of Dansyl-Polyamines. *J Chromatogr* 1990, 511, 177-183.
25. Soda, K.; Kano, Y.; Sakuragi, M.; Takao, K.; Lefor, A.; Konishi, F., Long-term oral polyamine intake increases blood polyamine concentrations. *J Nutr Sci Vitaminol* (Tokyo) 2009, 55 (4), 361-366.
26. Til, H. P.; Falke, H. E.; Prinsen, M. K.; Willems, M. I., Acute and subacute toxicity of tyramine, spermidine, spermine, putrescine and cadaverine in rats. *Food Chem Toxicol* 1997, 35 (3-4), 337-348.
27. Bolkenius, F. N.; Bey, P.; Seiler, N., Specific inhibition of polyamine oxidase in vivo is a method for the elucidation of its physiological role. *Biochim Biophys Acta* 1985, 838 (1), 69-76.

28. Cervelli, M.; Polticelli, F.; Fiorucci, L.; Angelucci, E.; Federico, R.; Mariottini, P., Inhibition of acetylpolyamine and spermine oxidases by the polyamine analogue chlorhexidine. *J Enzyme Inhib Med Chem* 2013, 28 (3), 463-7.

29. Di Paolo, M. L.; Cervelli, M.; Mariottini, P.; Leonetti, A.; Polticelli, F.; Rosini, M.; Milelli, A.; Basagni, F.; Venerando, R.; Agostinelli, E.; Minarini, A., Exploring the activity of polyamine analogues on polyamine and spermine oxidase: methoctramine, a potent and selective inhibitor of polyamine oxidase. *J Enzyme Inhib Med Chem* 2019, 34 (1), 740-752.

What is claimed is:

1. A spermine prodrug, wherein the spermine prodrug is 1a or 1b according to following formula:

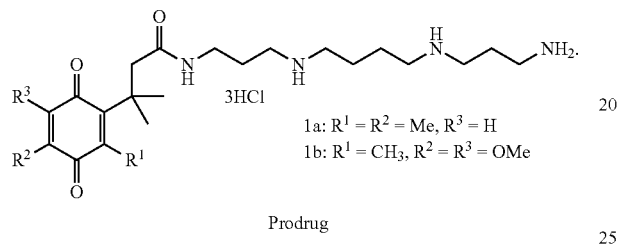

1a: $R^1 = R^2 = Me$, $R^3 = H$
1b: $R^1 = CH_3$, $R^2 = R^3 = OMe$

Prodrug

2. A composition comprising a spermine prodrug of claim 1, and a pharmaceutically acceptable carrier.

3. The composition of claim 2 formulated for oral administration.

4. The composition of claim 2 formulated for parenteral administration.

* * * * *